(12) United States Patent
Smith et al.

(10) Patent No.: US 9,486,321 B1
(45) Date of Patent: Nov. 8, 2016

(54) WEDGE-FIXING IMPLANT

(76) Inventors: Richard C. Smith, Rancho Palos Verdes, CA (US); Louis A. Serafin, Jr., Lakeport, MI (US)

( * ) Notice: Subject to any disclaimer, the term of this patent is extended or adjusted under 35 U.S.C. 154(b) by 946 days.

(21) Appl. No.: 12/287,378

(22) Filed: Oct. 8, 2008

Related U.S. Application Data

(60) Provisional application No. 60/998,198, filed on Oct. 9, 2007.

(51) Int. Cl.
*A61F 2/42* (2006.01)
*A61F 2/30* (2006.01)
*A61F 2/46* (2006.01)

(52) U.S. Cl.
CPC ............ *A61F 2/4202* (2013.01); *A61F 2/4657* (2013.01); *A61F 2/4684* (2013.01); *A61F 2002/30115* (2013.01); *A61F 2002/30138* (2013.01); *A61F 2002/30159* (2013.01); *A61F 2002/30398* (2013.01); *A61F 2002/30649* (2013.01); *A61F 2002/30879* (2013.01); *A61F 2002/30883* (2013.01); *A61F 2002/4205* (2013.01); *A61F 2002/4207* (2013.01); *A61F 2002/4623* (2013.01); *A61F 2250/0059* (2013.01); *A61F 2250/0064* (2013.01); *A61F 2310/00197* (2013.01)

(58) Field of Classification Search
CPC ........... A61F 2002/30387–2002/30388; A61F 2002/30883
USPC ................ 623/17.15, 21.18, 23.44
See application file for complete search history.

(56) References Cited

U.S. PATENT DOCUMENTS

| | | | |
|---|---|---|---|
| 3,840,904 A | 10/1974 | Tronzo | 3/1 |
| 3,889,300 A | 6/1975 | Smith | 3/1.91 |
| 3,965,489 A * | 6/1976 | Freeman et al. | 623/21.11 |
| 4,550,450 A | 11/1985 | Kinnett | 623/18 |
| 4,743,261 A * | 5/1988 | Epinette | 623/20.32 |
| 4,743,262 A | 5/1988 | Tronzo | 623/22 |
| 4,936,863 A | 6/1990 | Hofmann | 623/23 |
| 4,957,510 A | 9/1990 | Cremascoli | 623/23 |
| 5,007,932 A | 4/1991 | Bekki et al. | 623/18 |
| 5,037,440 A | 8/1991 | Koenig | 623/21 |
| 5,047,059 A | 9/1991 | Saffar | 623/21 |
| 5,314,486 A | 5/1994 | Zang et al. | 623/21 |
| 5,702,469 A | 12/1997 | Whipple et al. | 623/21 |
| 5,910,171 A | 6/1999 | Kummer et al. | 623/18 |

(Continued)

FOREIGN PATENT DOCUMENTS

EP 1707157 A1 * 10/2006 ............... A61F 2/36
WO WO 2004/080340 A2 9/2004

OTHER PUBLICATIONS

Brokenbrough, *Orthopedics Today*, "Decreased Pain, but 25% Complication Rate with Agility TAR," Apr. 2005, p. 60.

(Continued)

*Primary Examiner* — Yashita Sharma
*Assistant Examiner* — Rebecca Preston
(74) *Attorney, Agent, or Firm* — Christopher John Rudy; Vern D. Schooley

(57) ABSTRACT

Implant has an implant body; and connected to the body, a fin type stem adapted for transverse insertion into a bodily substrate. The stem has a laterally disposed feature for providing stopping of the stem along a path it takes in its insertion into the substrate. For example, the laterally disposed feature can embrace a wedge. Tools and kits are provided for or with the implant.

26 Claims, 40 Drawing Sheets

(56) References Cited

U.S. PATENT DOCUMENTS

| | | | | |
|---|---|---|---|---|
| 6,102,953 | A * | 8/2000 | Huebner | 623/19.11 |
| 6,299,647 | B1 | 10/2001 | Townley | 623/22.32 |
| 6,454,809 | B1 * | 9/2002 | Tornier | 623/22.32 |
| 7,476,255 | B2 * | 1/2009 | Lester et al. | 623/23.15 |
| 2002/0055784 | A1 * | 5/2002 | Burstein et al. | 623/20.28 |
| 2003/0208273 | A1 * | 11/2003 | Eisermann et al. | 623/17.14 |
| 2003/0233147 | A1 * | 12/2003 | Nicholson et al. | 623/17.16 |
| 2004/0167631 | A1 * | 8/2004 | Luchesi et al. | 623/21.18 |
| 2004/0193268 | A1 * | 9/2004 | Hazebrouck | 623/16.11 |
| 2005/0143834 | A1 * | 6/2005 | Lester | A61B 17/15 623/22.4 |
| 2006/0025866 | A1 * | 2/2006 | Serafin et al. | 623/23.56 |
| 2006/0195196 | A1 * | 8/2006 | Pendleton et al. | 623/20.34 |
| 2006/0229732 | A1 * | 10/2006 | Bachelier | 623/22.42 |
| 2009/0082875 | A1 * | 3/2009 | Long | 623/21.18 |
| 2010/0145461 | A1 * | 6/2010 | Landry et al. | 623/17.16 |
| 2010/0217395 | A1 * | 8/2010 | Bertagnoli | A61B 17/14 623/17.16 |

OTHER PUBLICATIONS

Hintermann et al., American Academy of Orthopaedic Surgeons 72nd Annual Meeting Instructional Course Lecture Handout, "Total Ankle Arthroplasty: Current State of Art," Feb. 23, 2005.
Lamb, *J. Bone & Jt. Surgery*, "The Ball and Socket Ankle Joint—a Congenital Abnormality." vol. 408, No. 2, May 1958, pp. 240-243.
Saltzman, *Orthopedics Today*, Round Table, "Ankle Fusion and Total Ankle Replacement: Making the Right Choices, How Top Physicians Make the Call," Apr. 2005, pp. 64, 66, 68 & 70.
Smith, Orthopedic Seminars, University of Southern California Department of Orthopedic Surgery, "Total Ankle Replacement, a Case Presentation," 1972 vol. V, Sep. 9, 1972, pp. 405-407.
Wright Mfg. Co., Smith Total Ankle, 1975, four pages, plus three sheets of engineering prints from 1972.
BioPro, Inc., Port Huron, Mich., "Metallic Hemiarthroplasty Resurfacing Prosthesis for the Hallux Metatarsophalangeal Joint," Surgical Technique, Brochure No. 06053, ca. 1995, 2 pages.
BioPro, Inc., Port Huron, Mich., Products>LowerExtremities> Great Toe Hemi Implant, 2010, 1 page; "Hemi Implant," Literature, Brochure No. 16391 Rev2, 2010, 2 pages; "Metallic Hemiarthroplasty Resurfacing Prosthesis for the Hallux Metatarsophalangeal Joint," Surgical Technique, Brochure No. 16953, 2010, 2 pages—all downloaded Mar. 9, 2010.
BioPro, Inc., Port Huron, Mich., Products>UpperExtremities> Modular Basal Thumb Implant, 2010, 1 page; "Thumbs Up," Literature, Brochure No. 17367 rev4, 2 pages, 2010; "Modular Thumb Implant," Surgical Technique, Brochure No. 17498 rev2, 2010, 8 pages—all downloaded Mar. 9, 2010.
BioPro, Inc., Port Huron, Mich., "PSL Physiological Stress Loading Total Hip Replacement System Utilizing the Horizontal Platform Supported Concept," Surgical Technique, Mar. 1998.
BioPro, Inc., Port Huron, Mich., "The BioPro Ceramic Tara," ca. Oct. 1997, 2 pages.
Prichett, James W., "Curved-stem Hip Resurfacing," Clin Orthop Relat Res 2008, vol. 466, pp. 1177-1185.
Signal Medical Corporation, SMC Great Toe, May 6, 2002, 1 page.
Wright Medical, "Swanson Titanium Basal Thumb Implant," Product Literature/Brochure, prior to 1999, 7 pages.
Richard C. Smith, Smith Talar Prosthesis (Wright Manufacturing Company), 1974.
Espinoza, N., et al., "Misalignment of Total Ankle Components Can Induce High Joint Contact Pressures," J. Bone & Joint Surgery Am., May 2010; 92(5) 1179-1187 (Astract).
Easley, M., et al., "Total Ankle Arthroplasty," J. Am. Ac. Orthopaedic Surgeons, vol. 10, No. 3, May/Jun. 2002, pp. 157-167.
Gray, H., Gray's Anatomy, 1901 Ed., Barnes & Noble 1995, p. 172.
Tornier, Inc., "Salto Talaris™ Total Ankle Prosthesis," 2014, 2 pp.

* cited by examiner

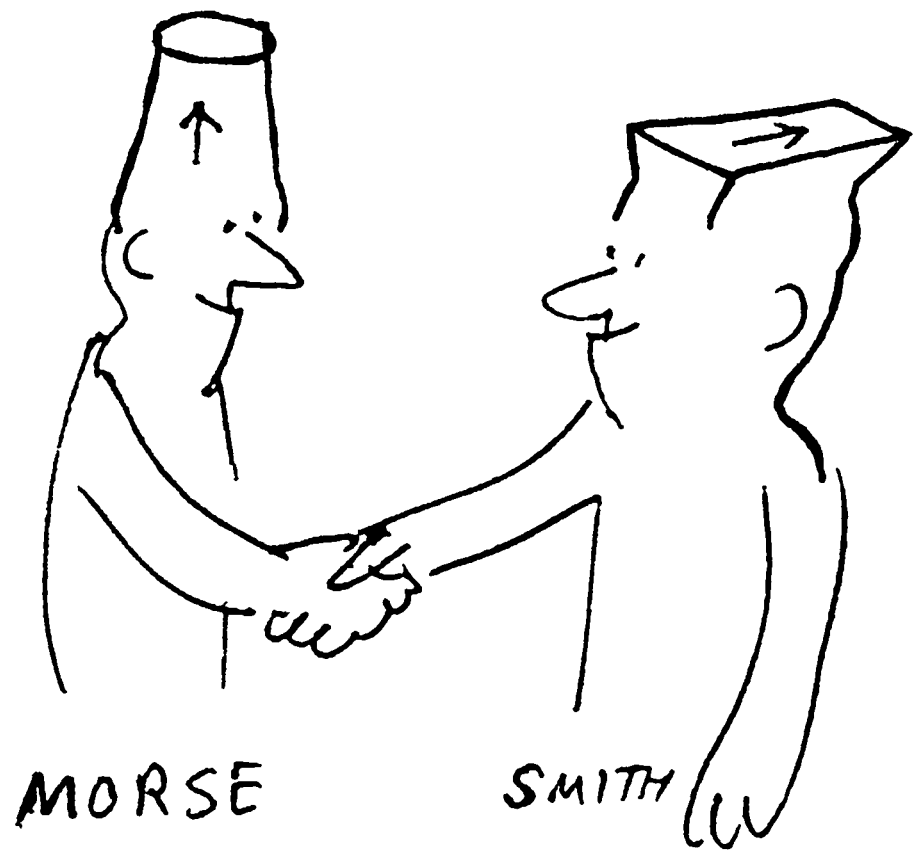

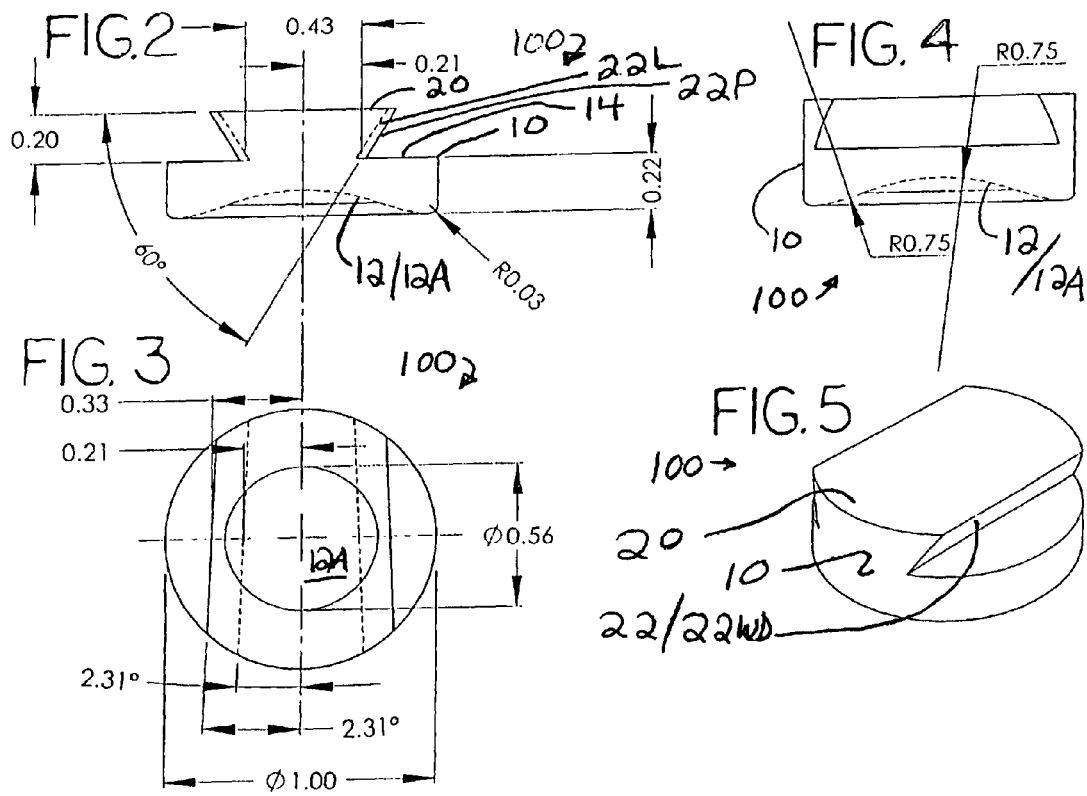
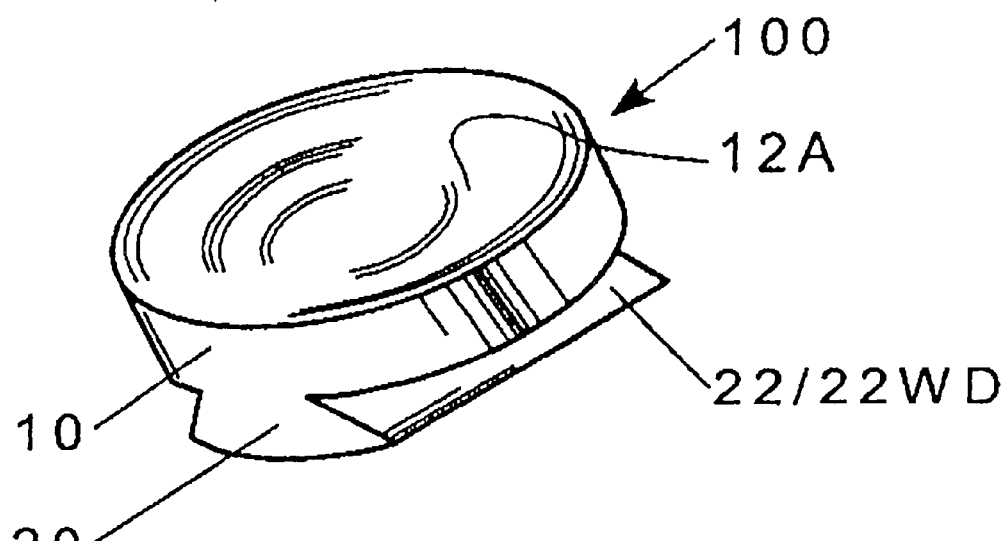
Fig. 6

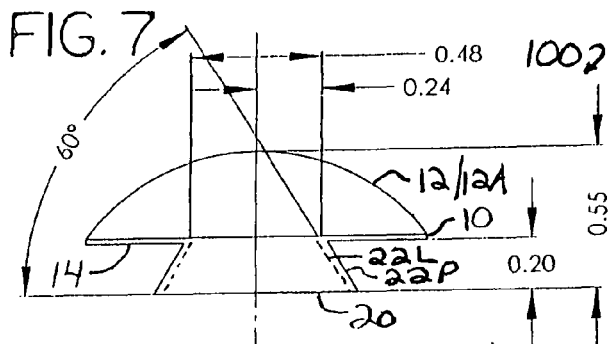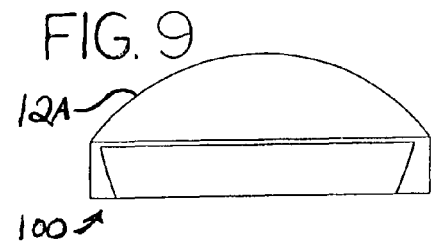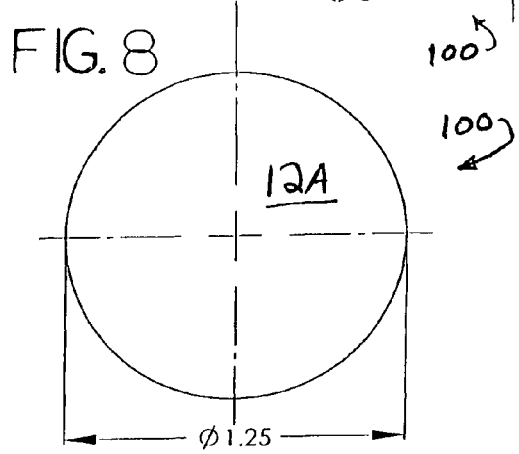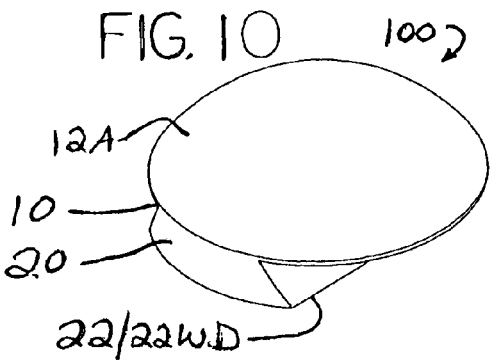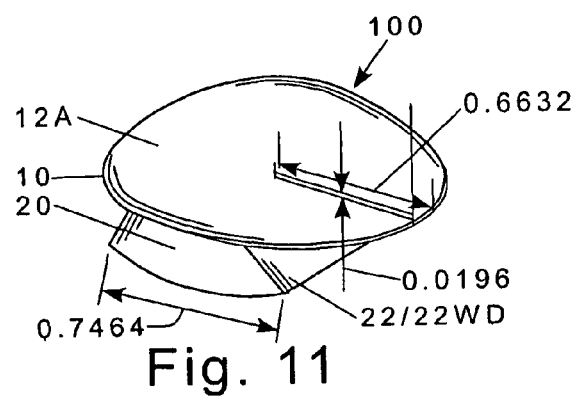

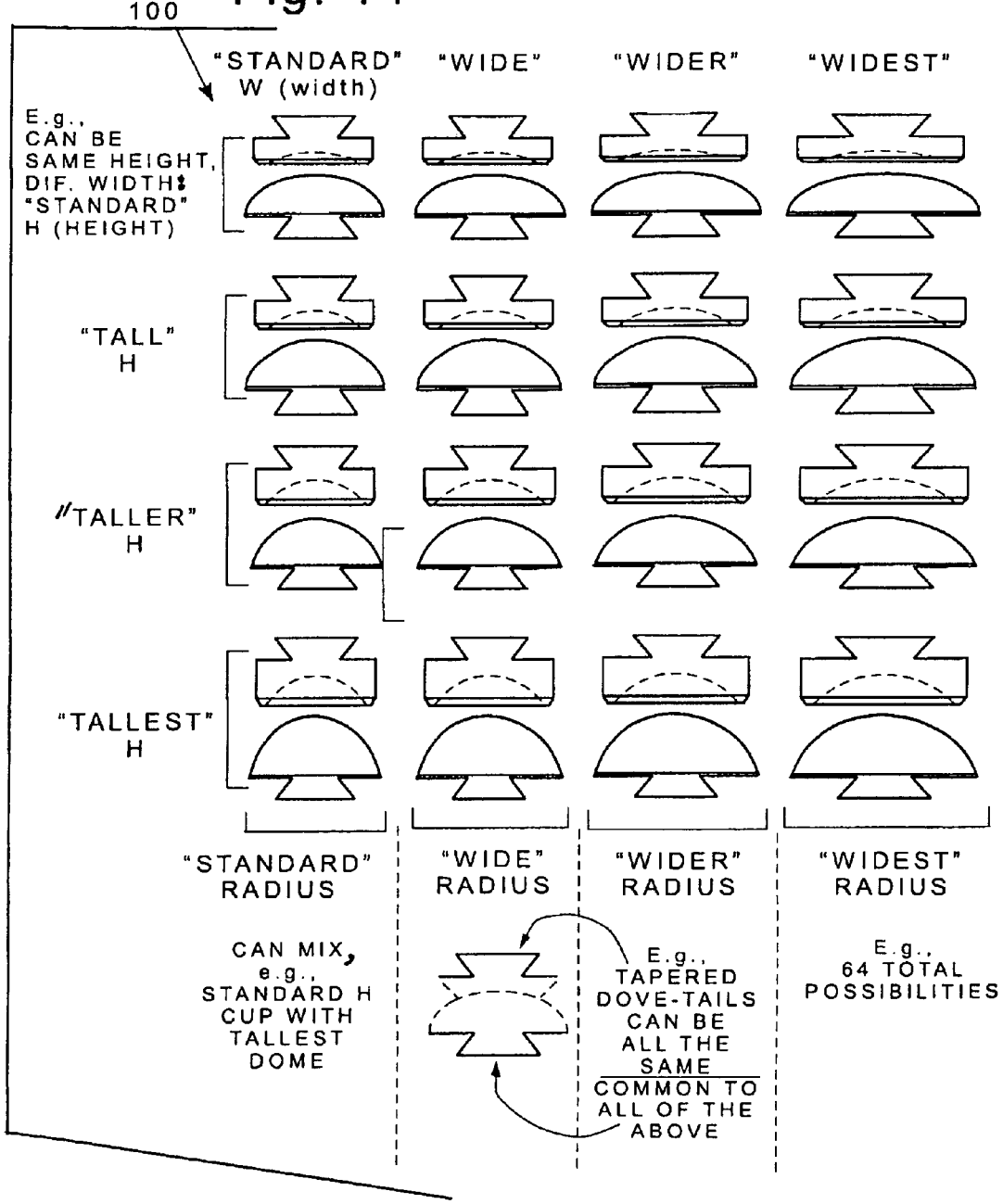

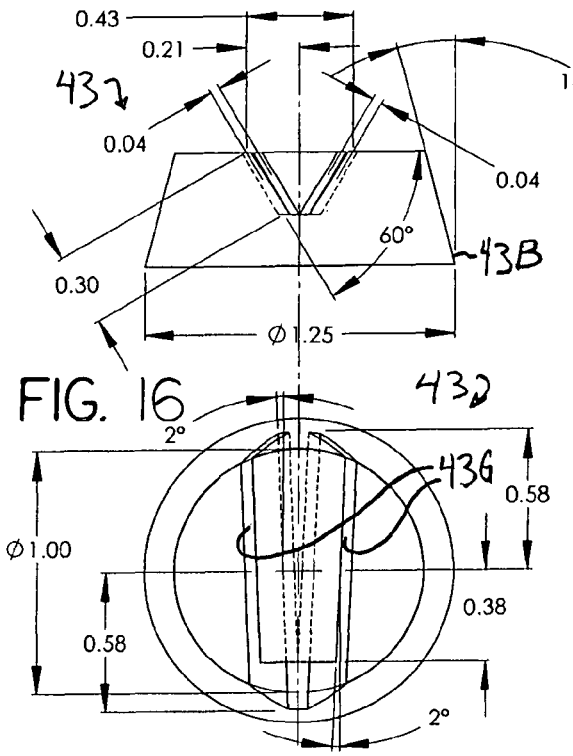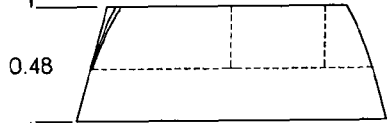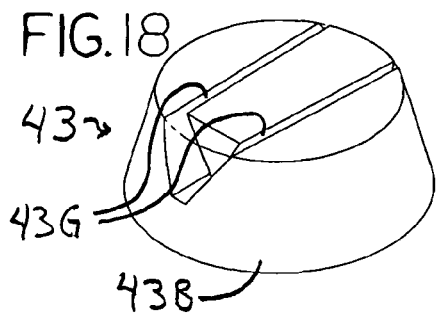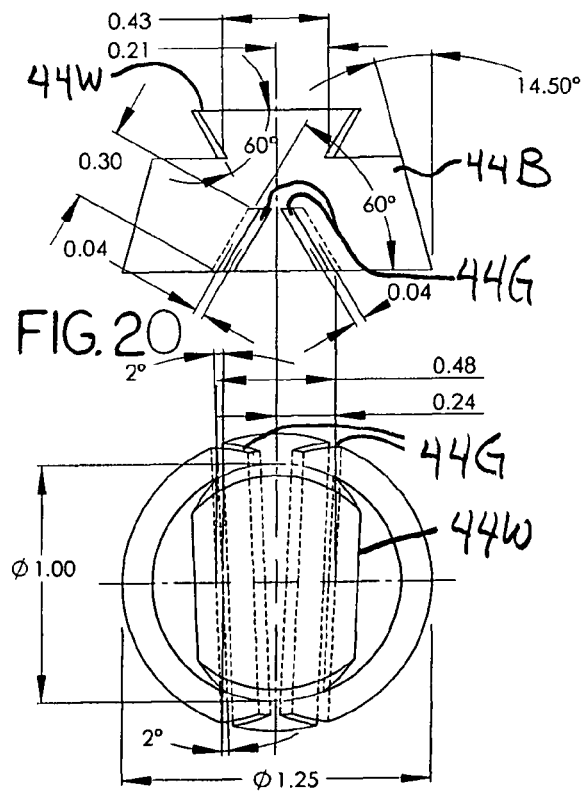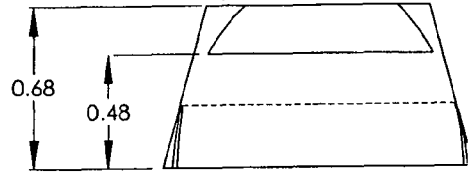

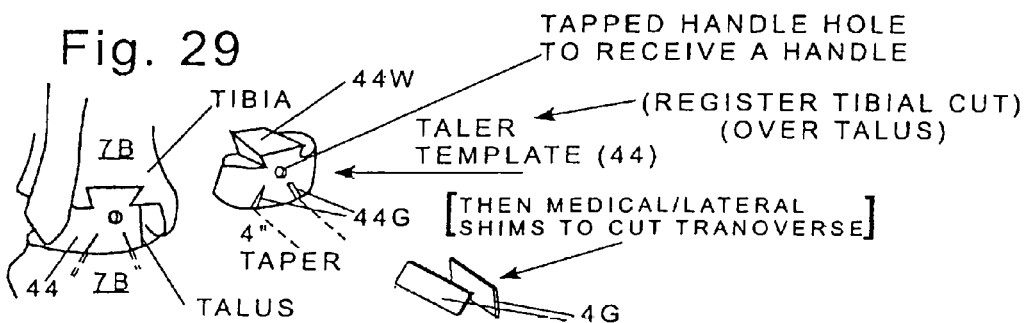
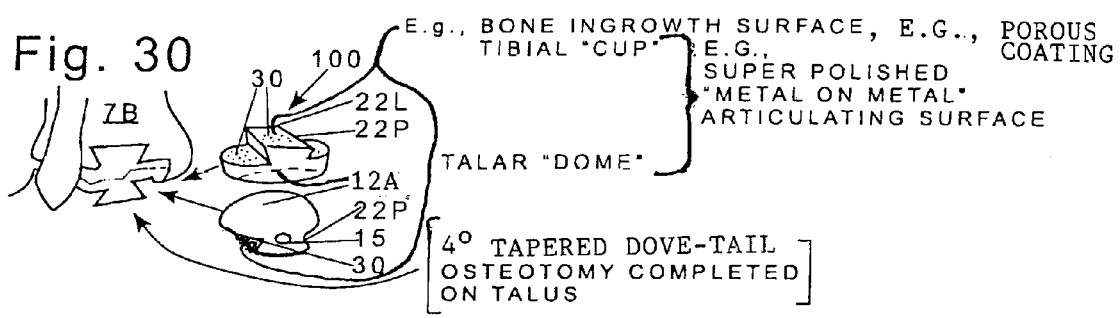
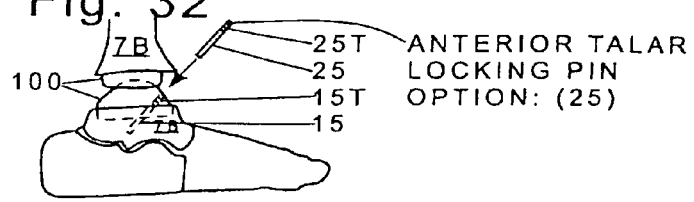

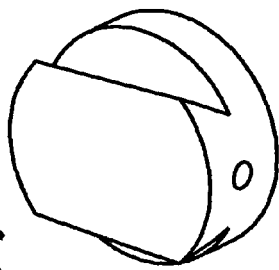
FIG. 39
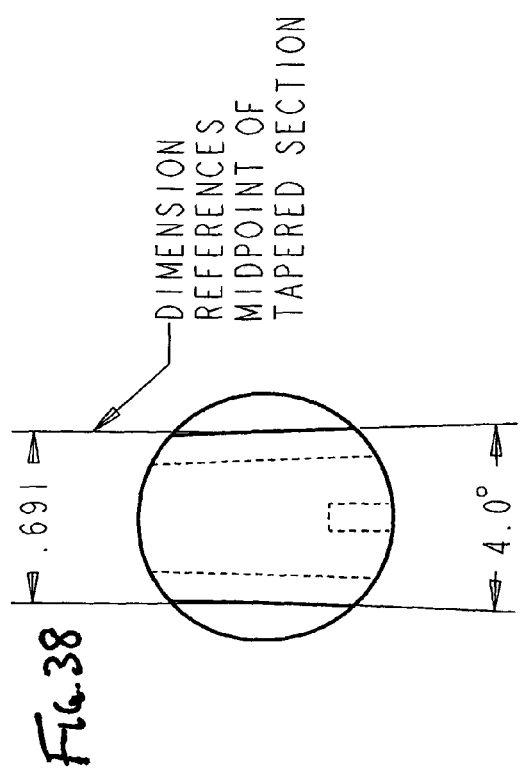
FIG. 38
FIG. 40
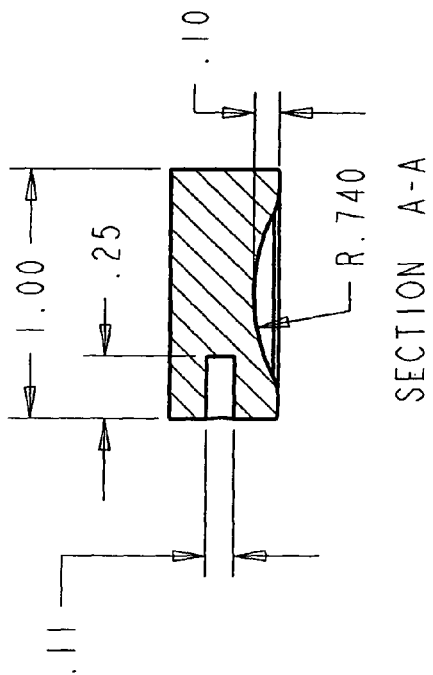
FIG. 41
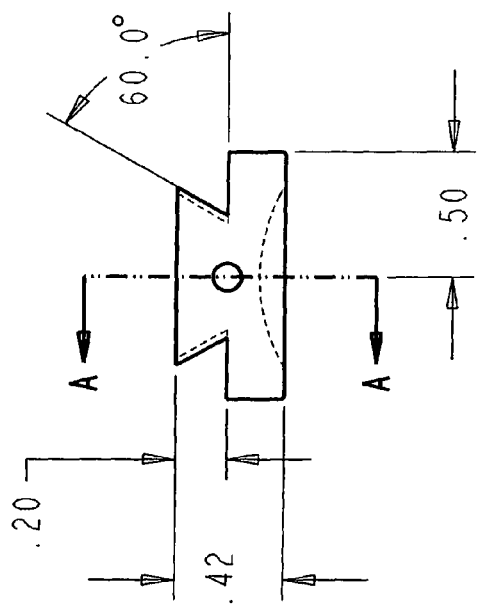

SECTION A-A

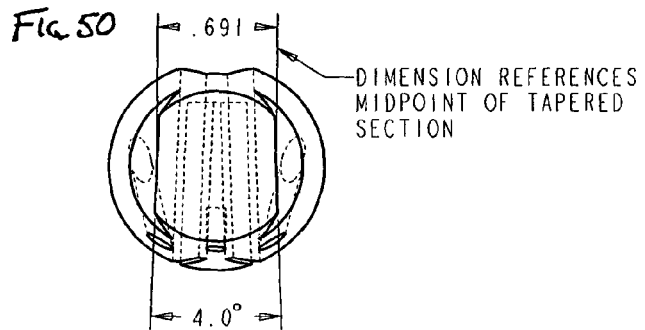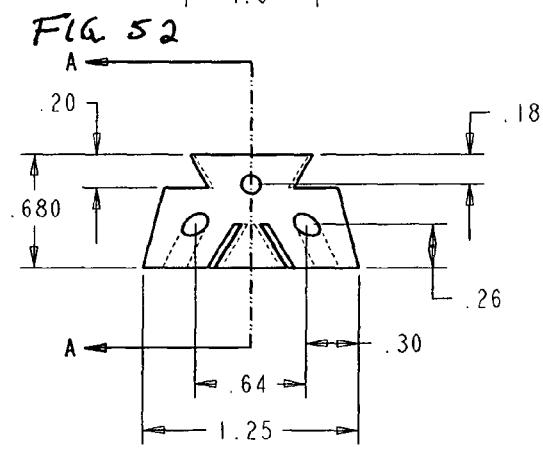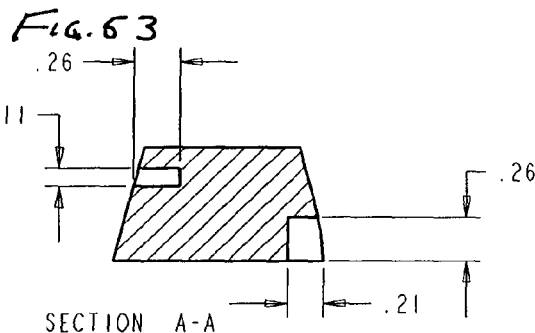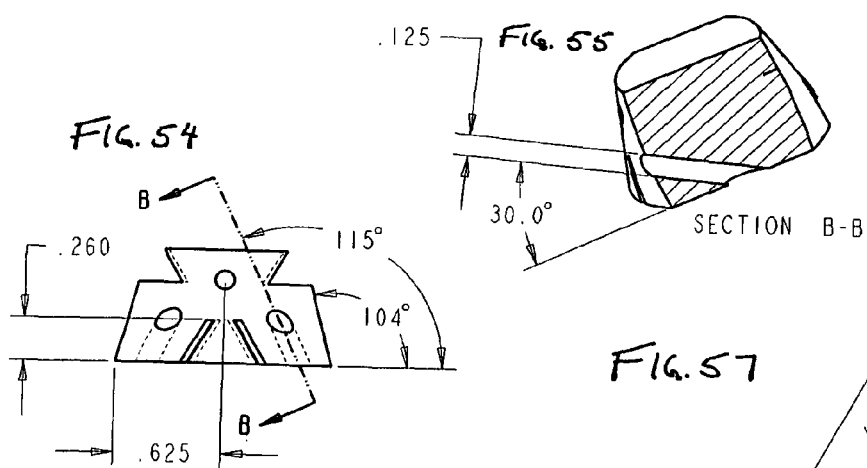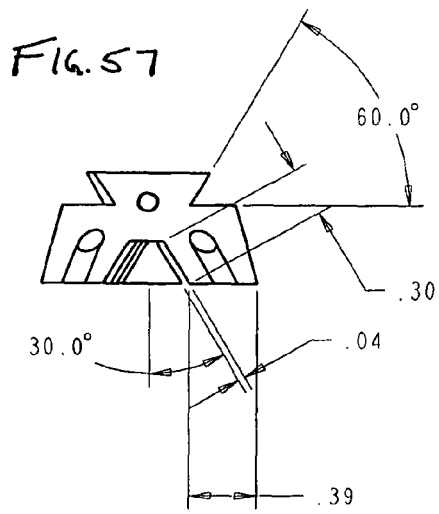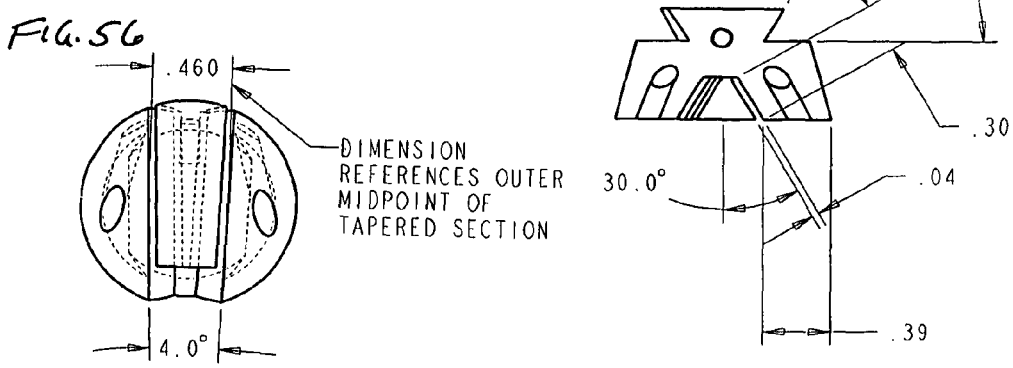

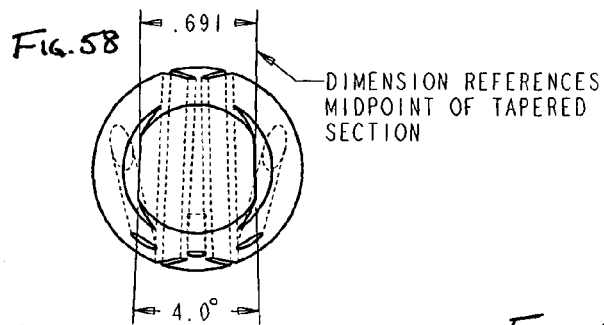
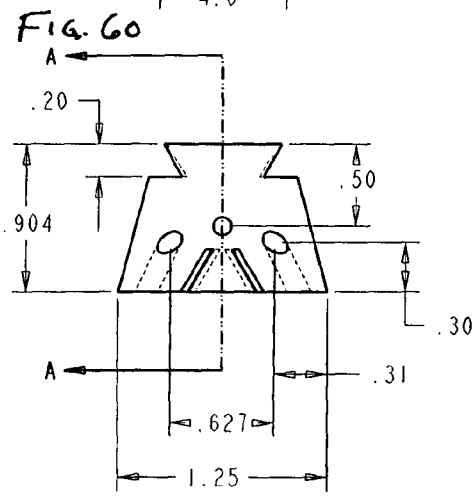
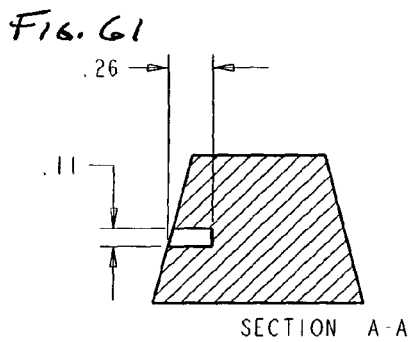
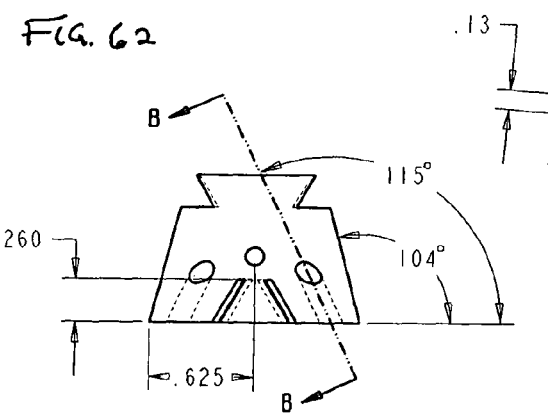
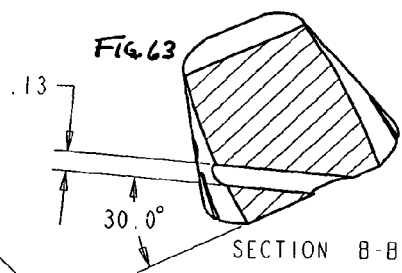
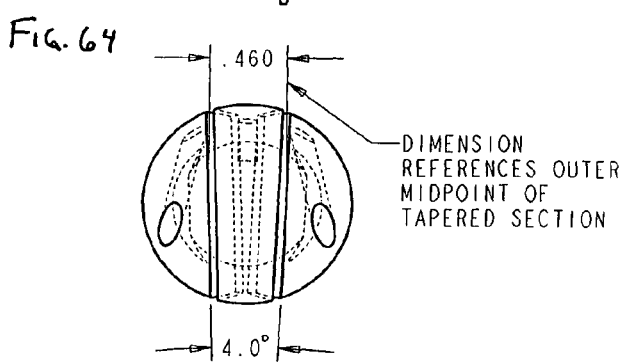
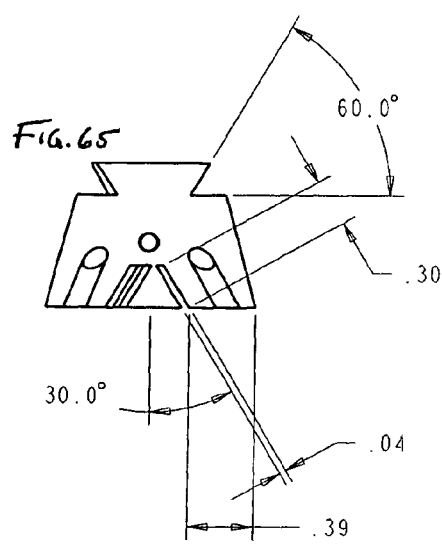

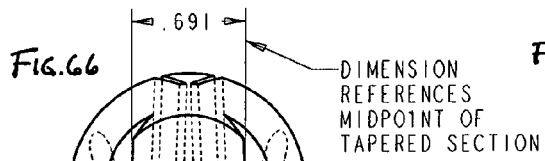
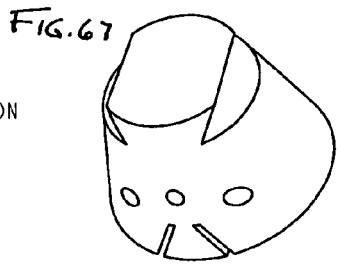
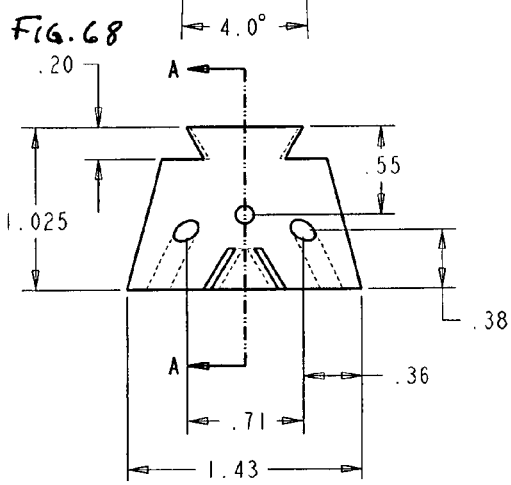
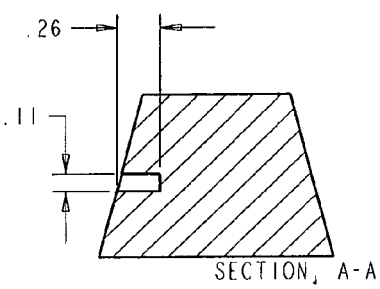
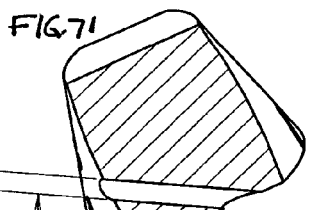
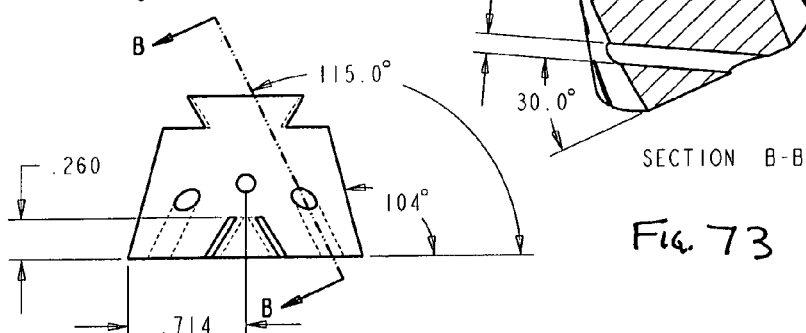
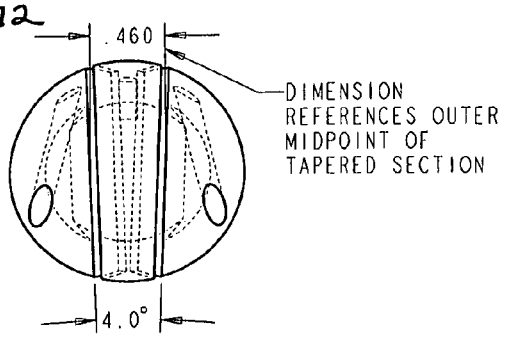
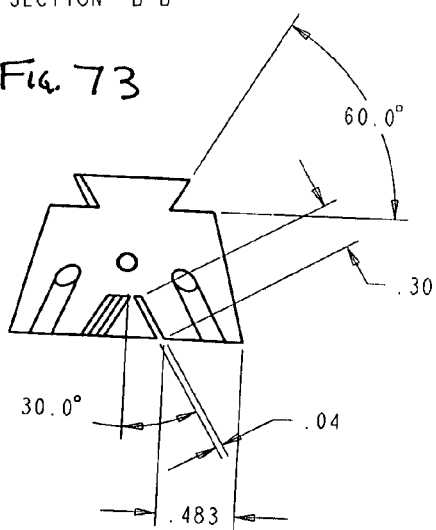

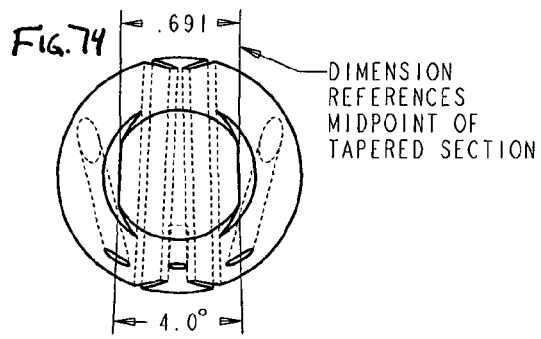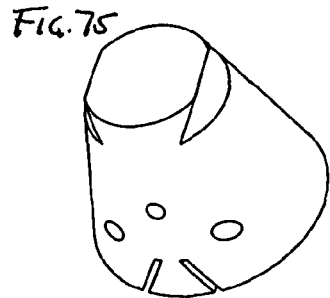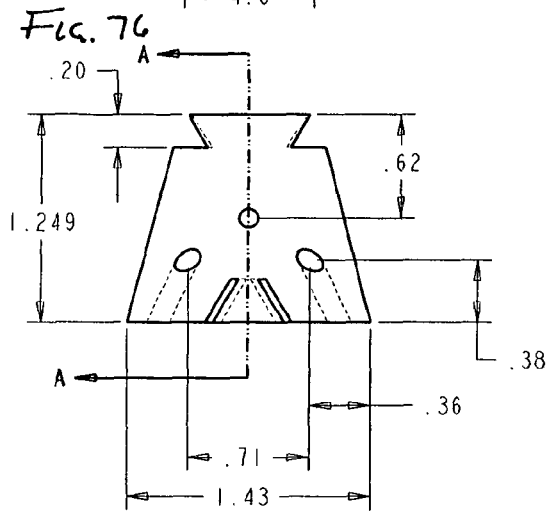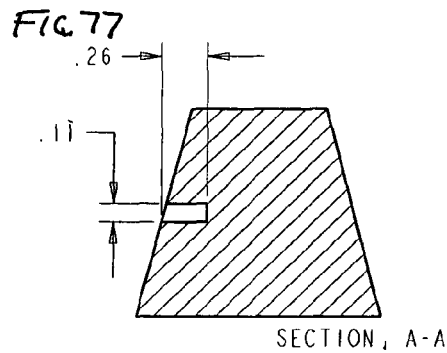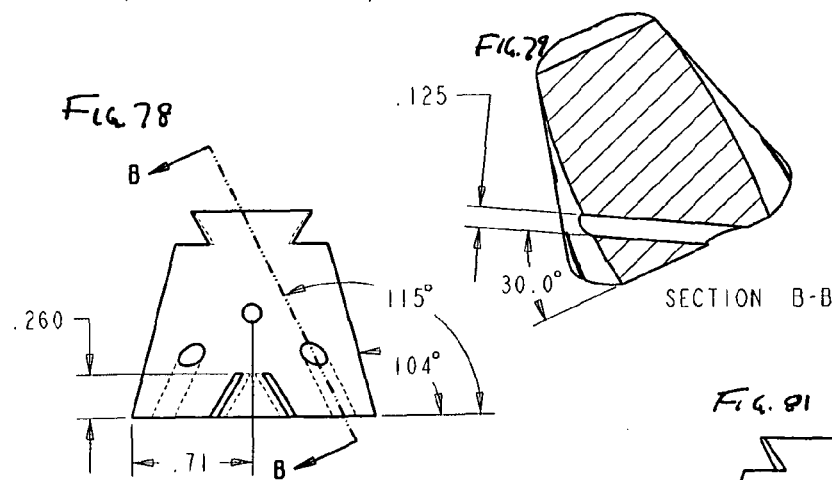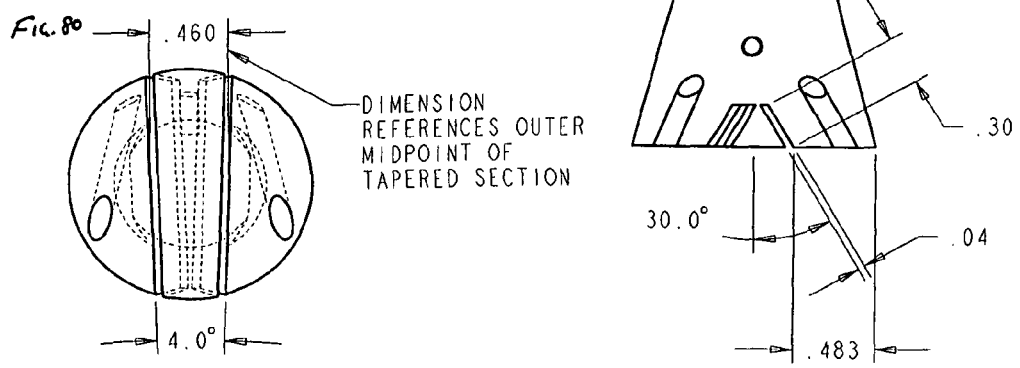

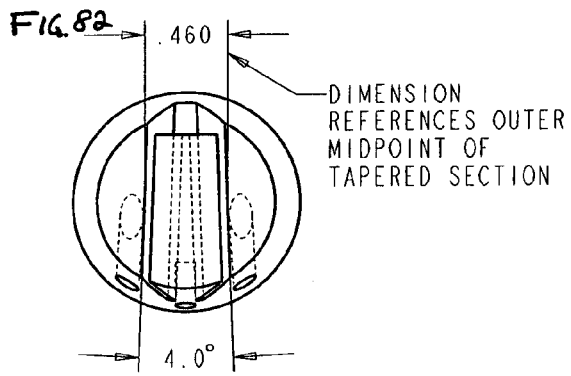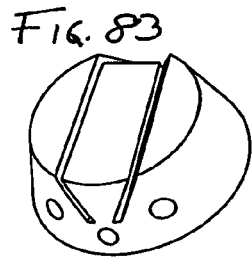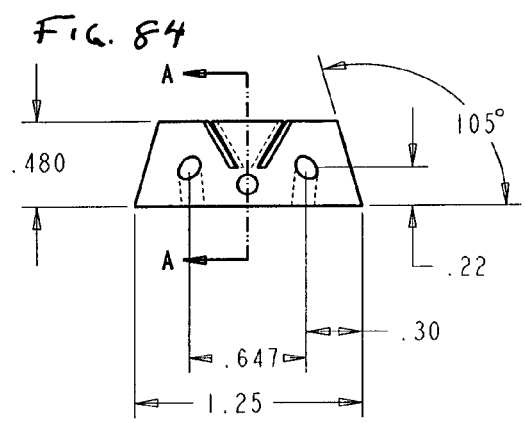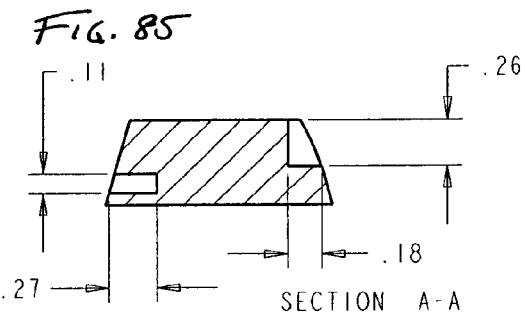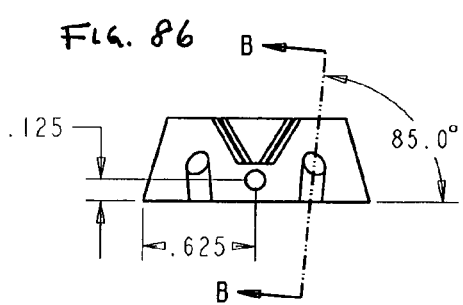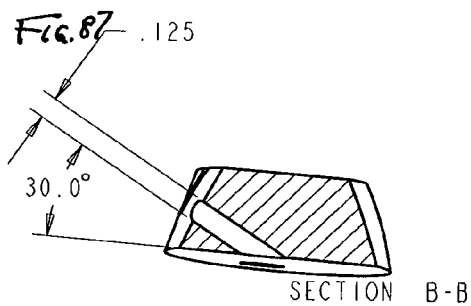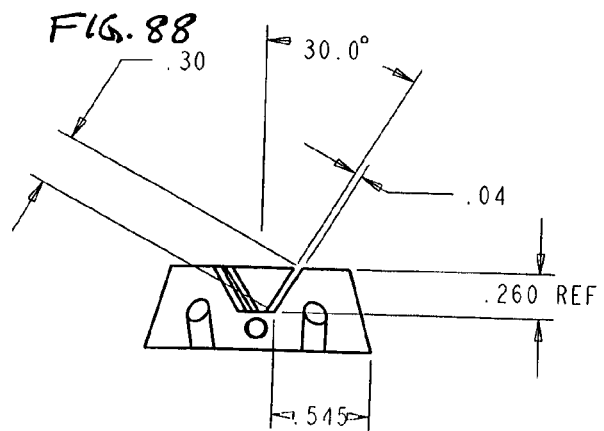

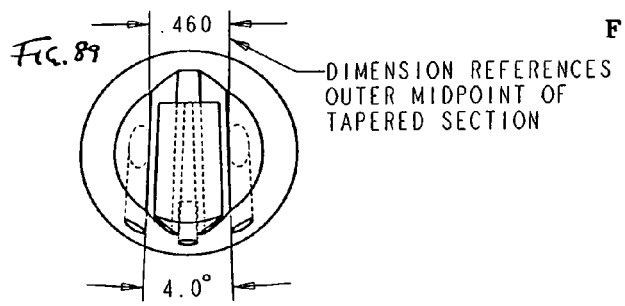
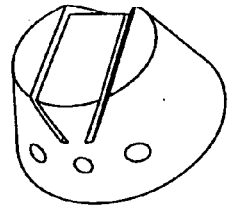
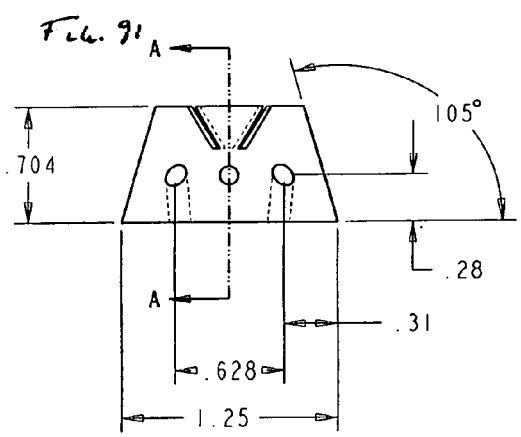
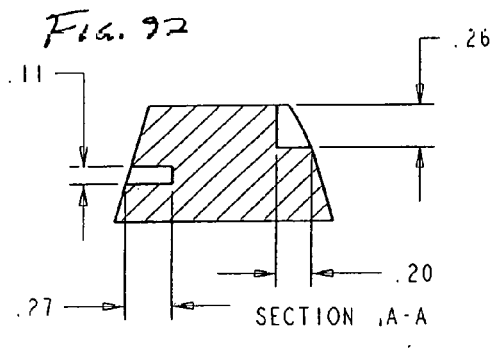
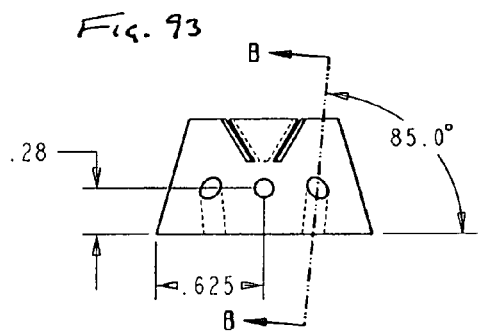
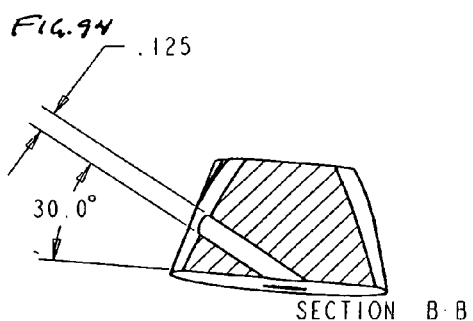
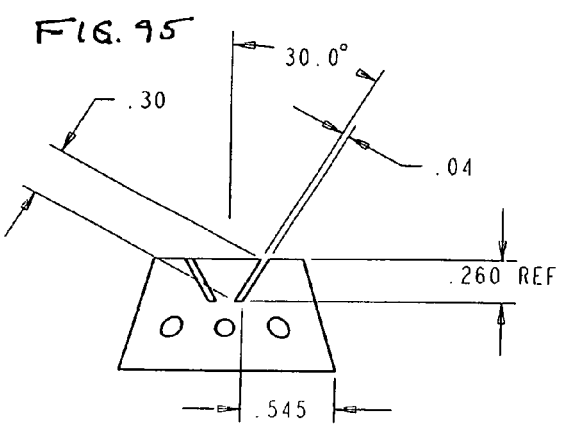

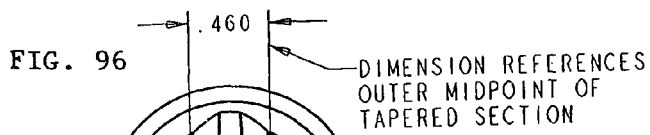
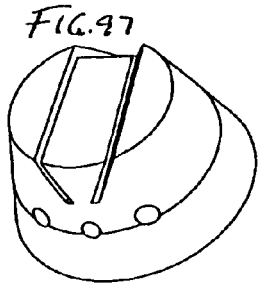
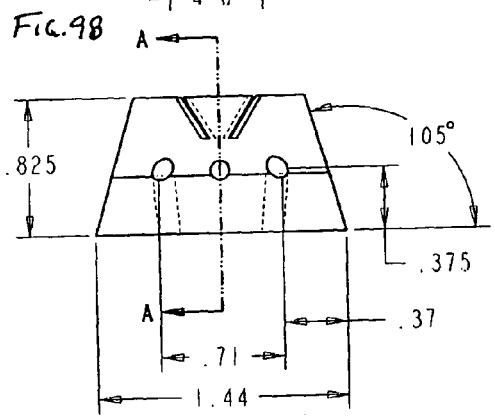
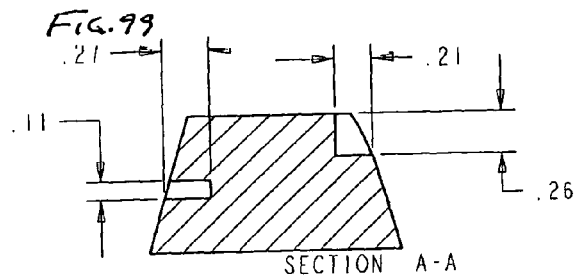
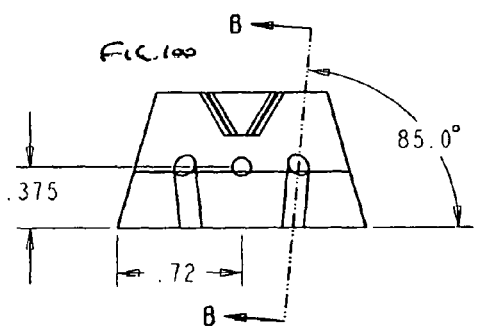
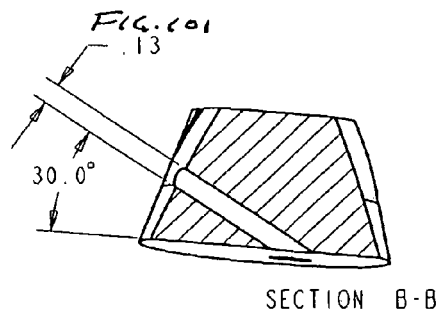
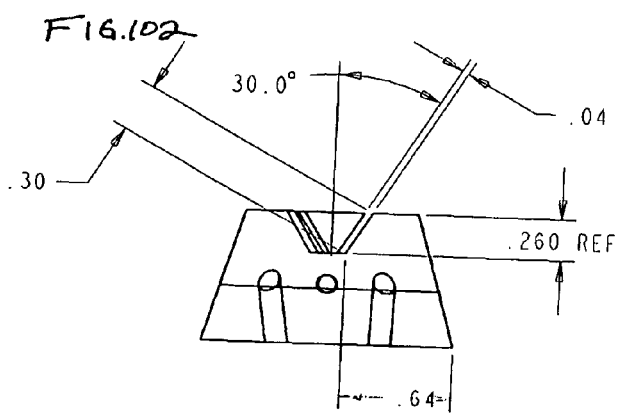

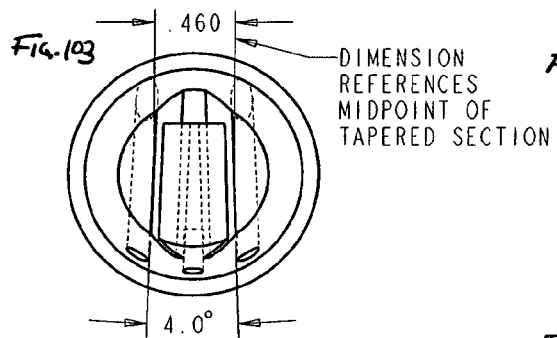
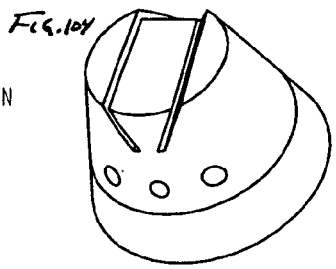
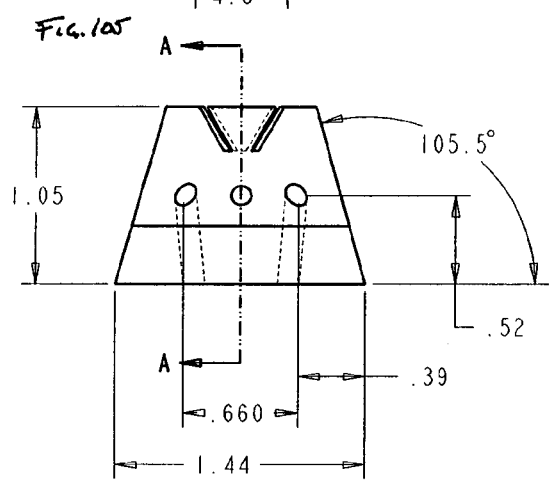
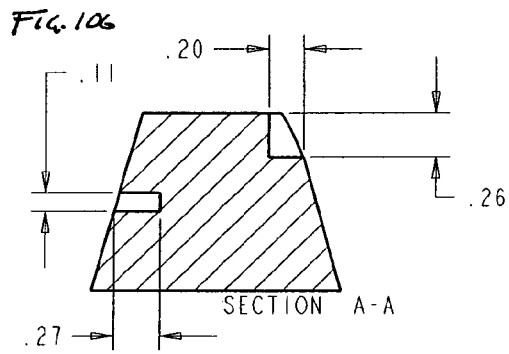
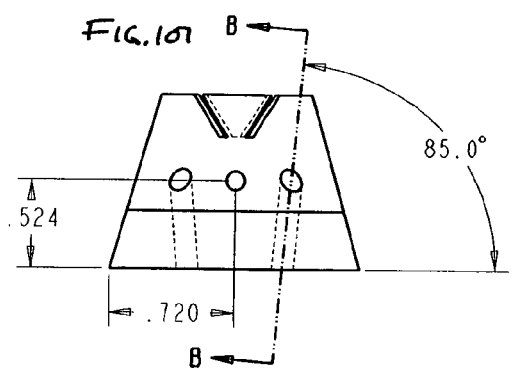
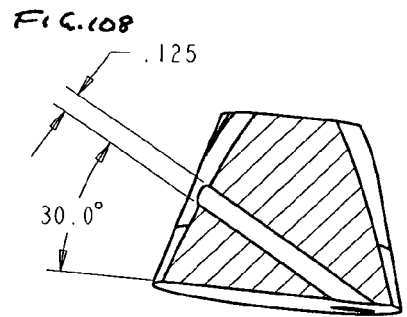
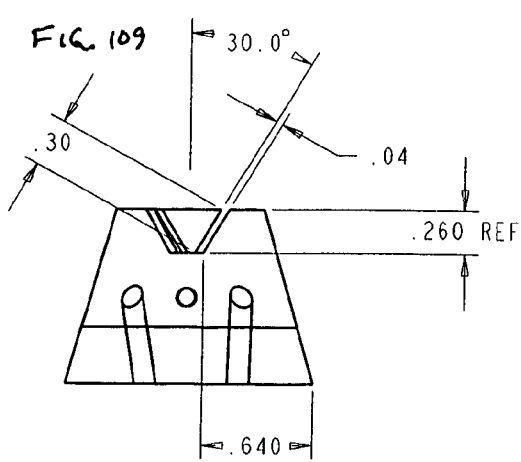

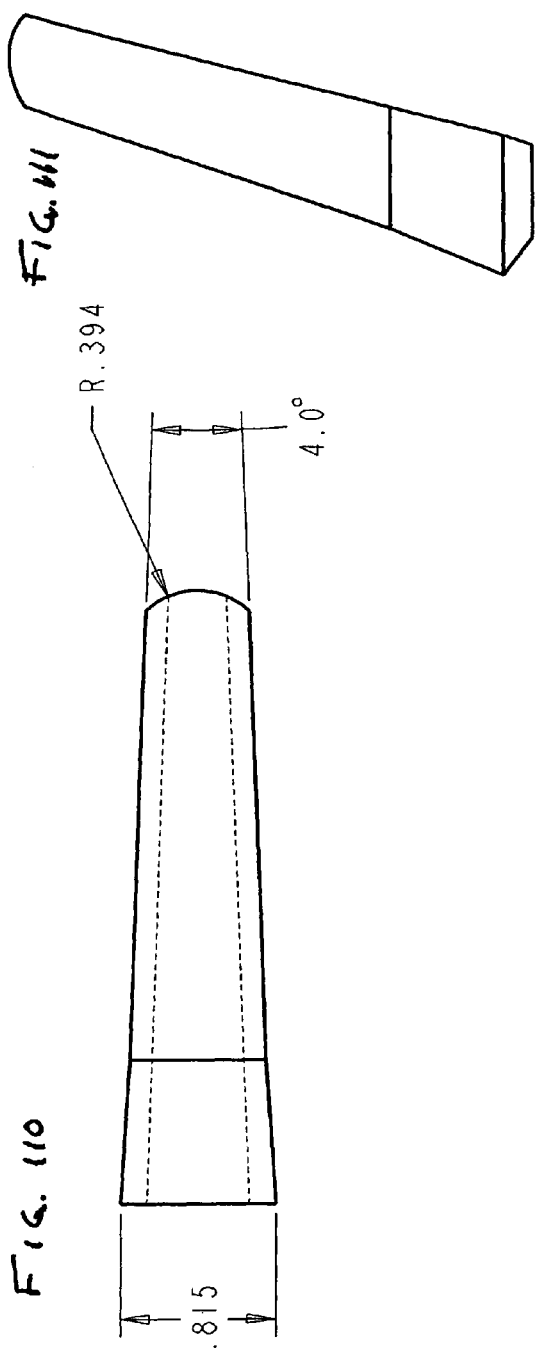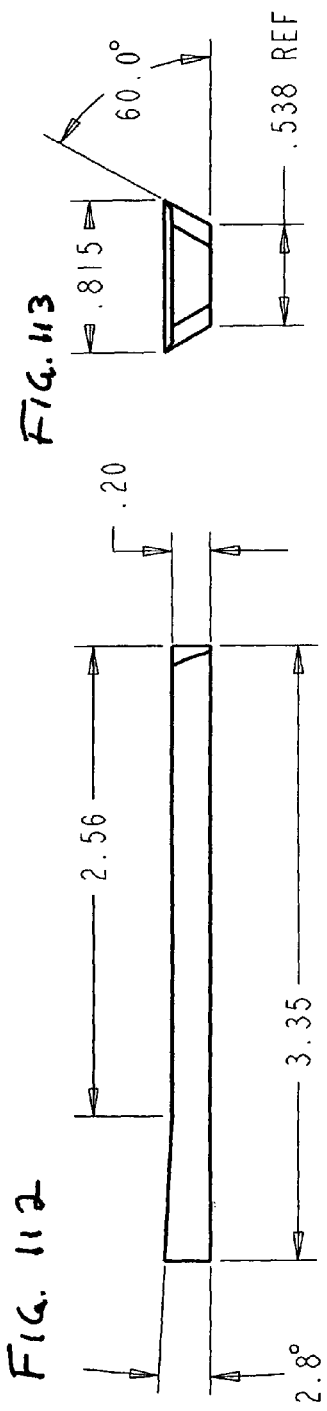
NOTE: ADD RASPS ON EACH OF THE FOUR LONG SIDES OF THE PART VIA EDM BURNING

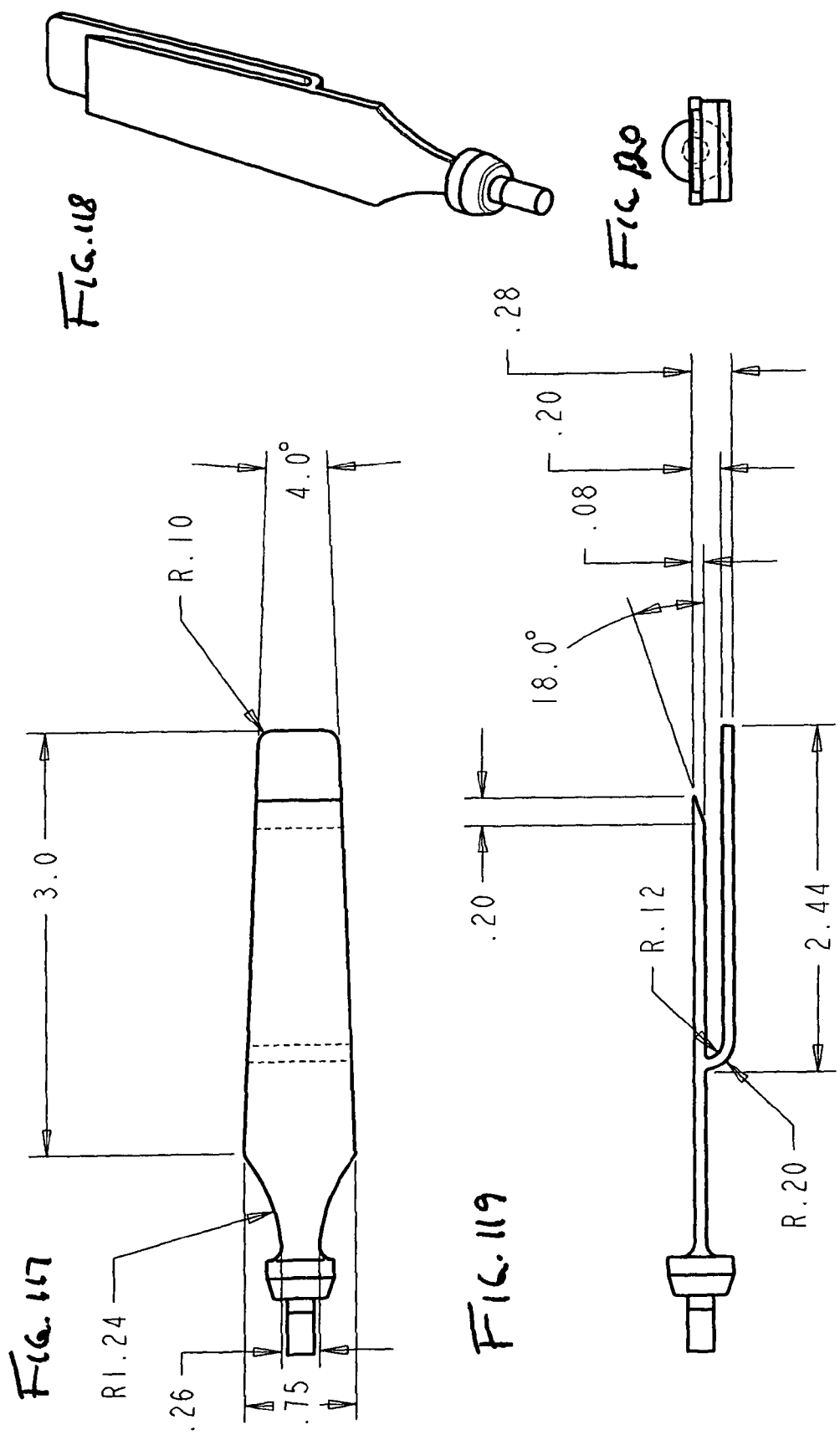

SECTION A-A

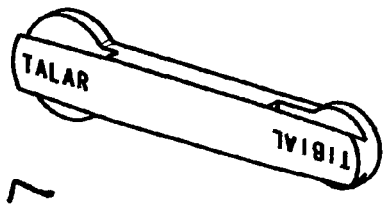
FIG. 127
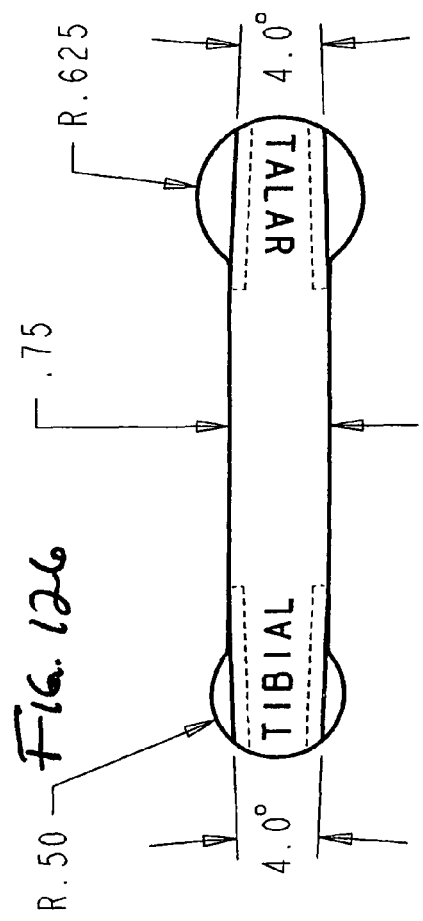
FIG. 126
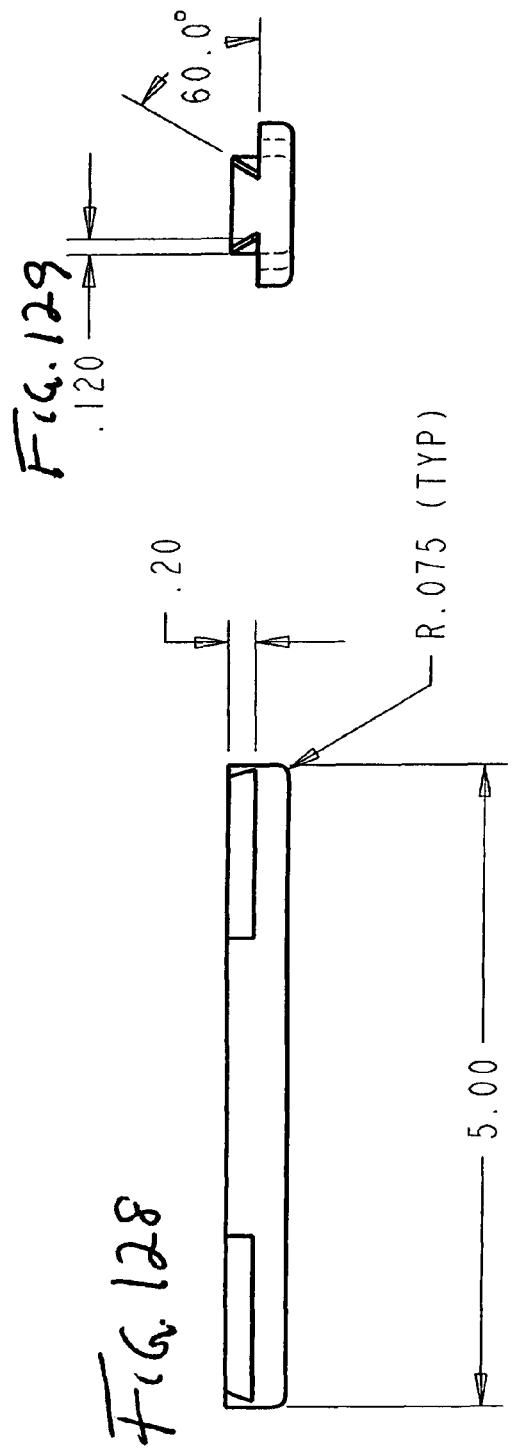
FIG. 129
FIG. 128

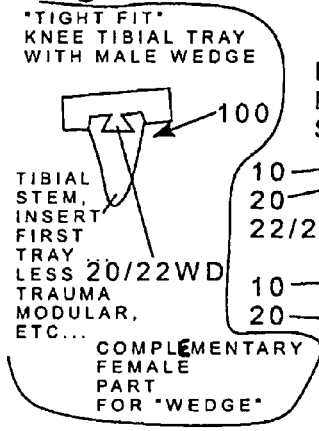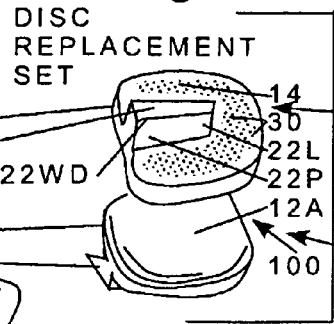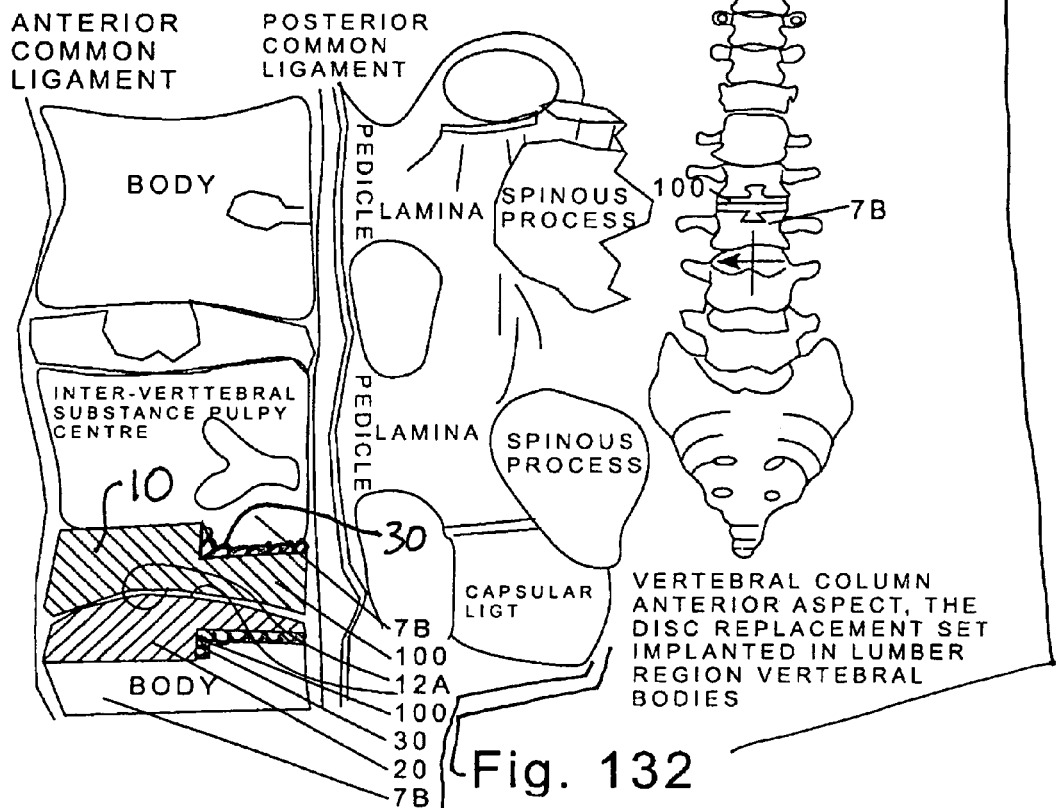

Fig. 130 "TIGHT FIT" KNEE TIBIAL TRAY WITH MALE WEDGE
TIBIAL STEM, INSERT FIRST TRAY LESS 20/22WD TRAUMA MODULAR, ETC...
COMPLEMENTARY FEMALE PART FOR "WEDGE"

Fig. 131 DISC REPLACEMENT SET
UPPER
LOWER

Fig. 132 VERTEBRAL COLUMN ANTERIOR ASPECT, THE DISC REPLACEMENT SET IMPLANTED IN LUMBER REGION VERTEBRAL BODIES

Fig. 133 VERTICAL SECTION OF THE DISC REPLACEMENT SET, IMPLANTED IN ADJACENT VERTEBRAL BODIES FROM THE LUMBAR REGION

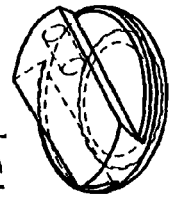
Fig.134
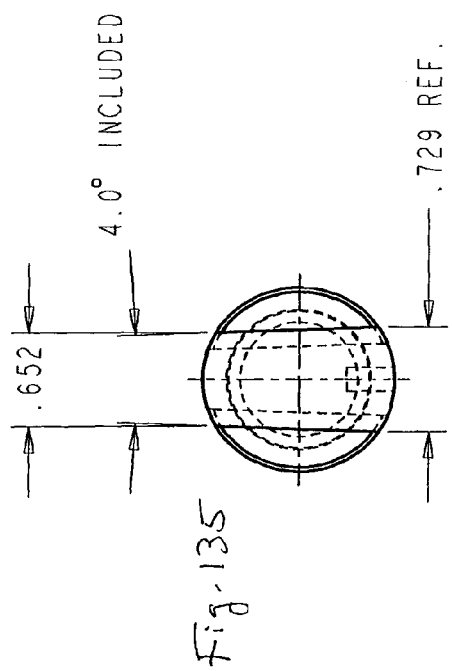
Fig.135
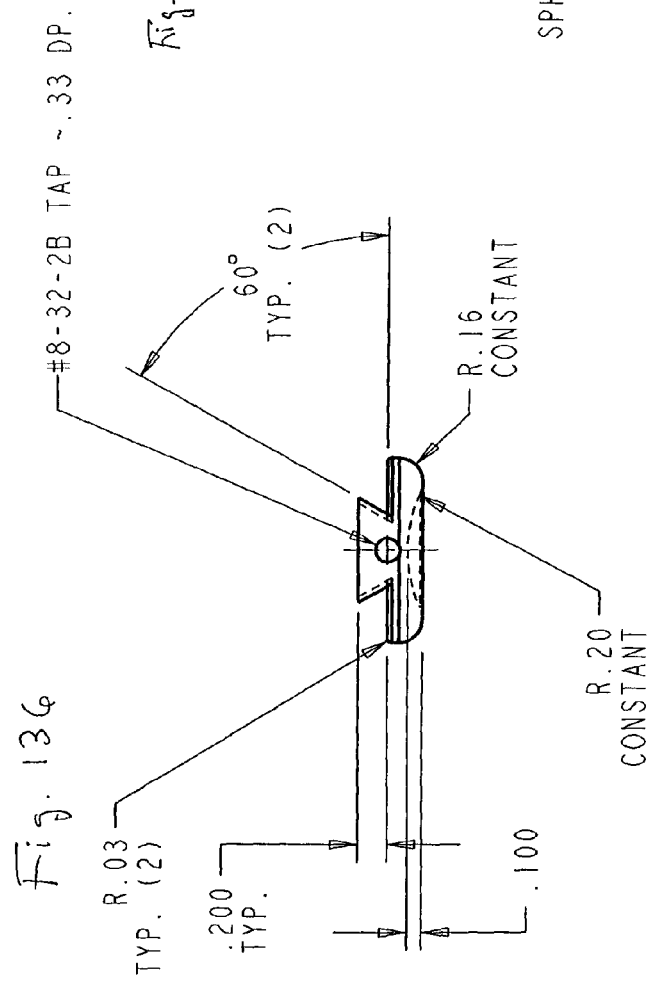
Fig.136
Fig.137

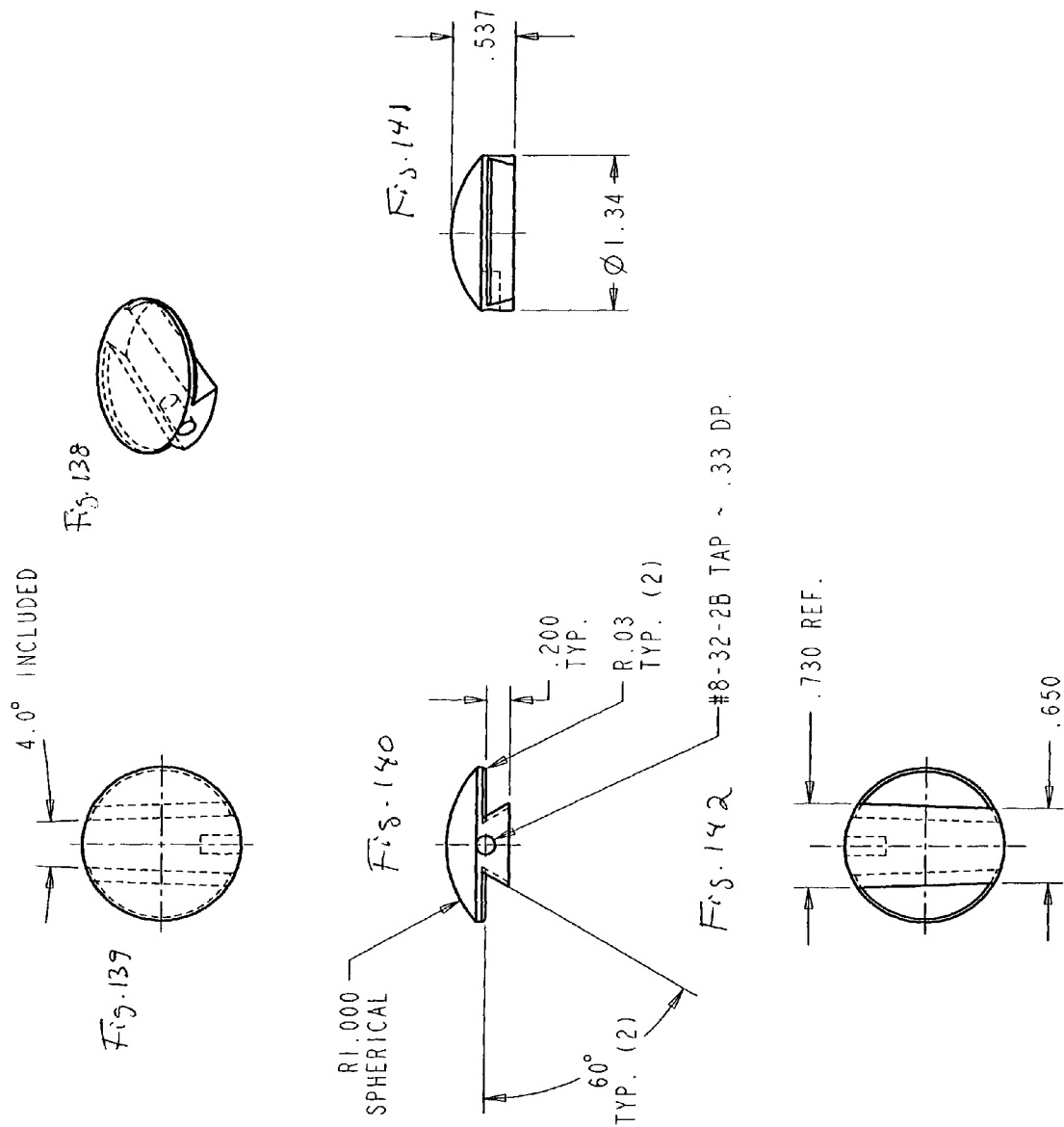

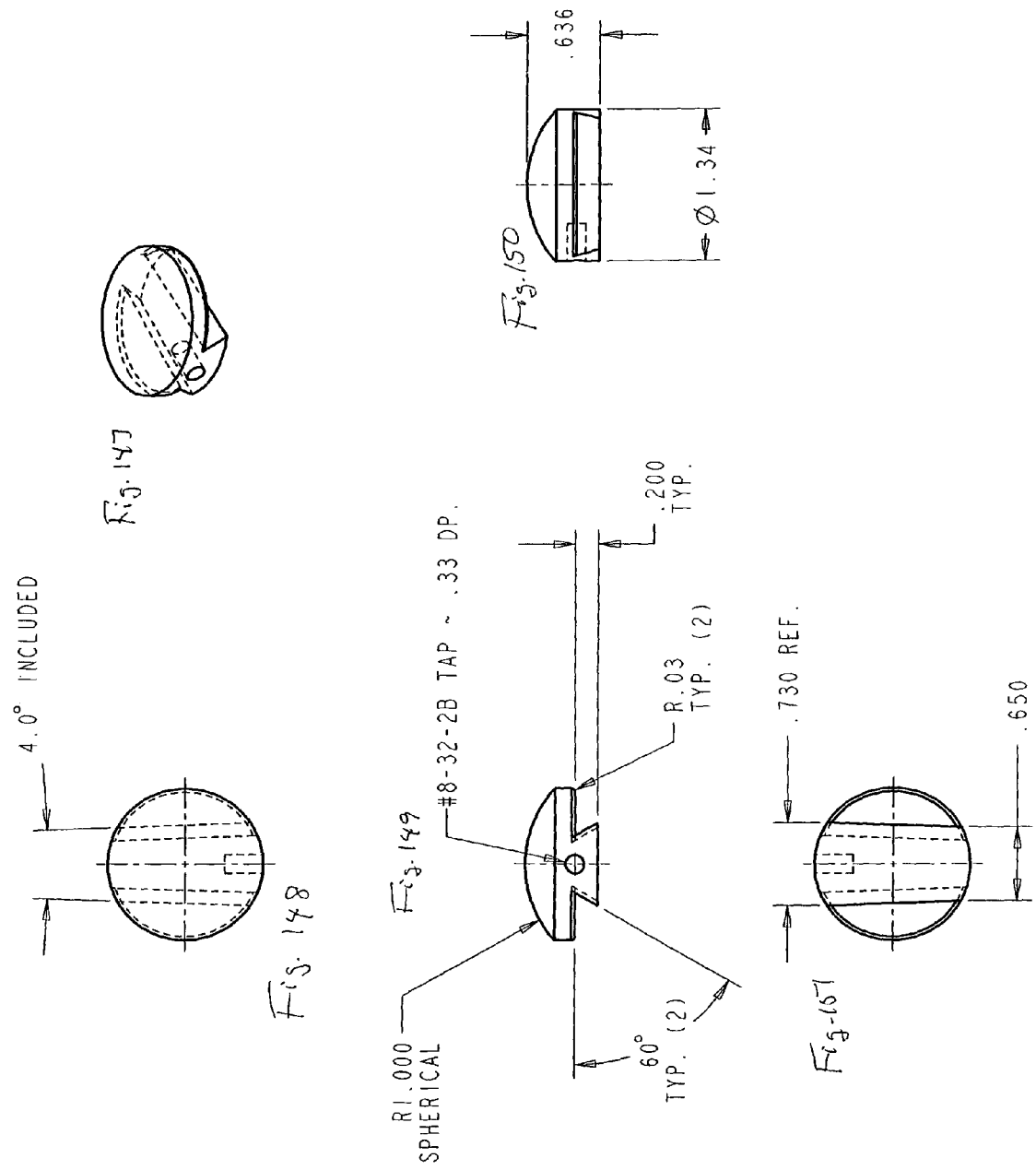

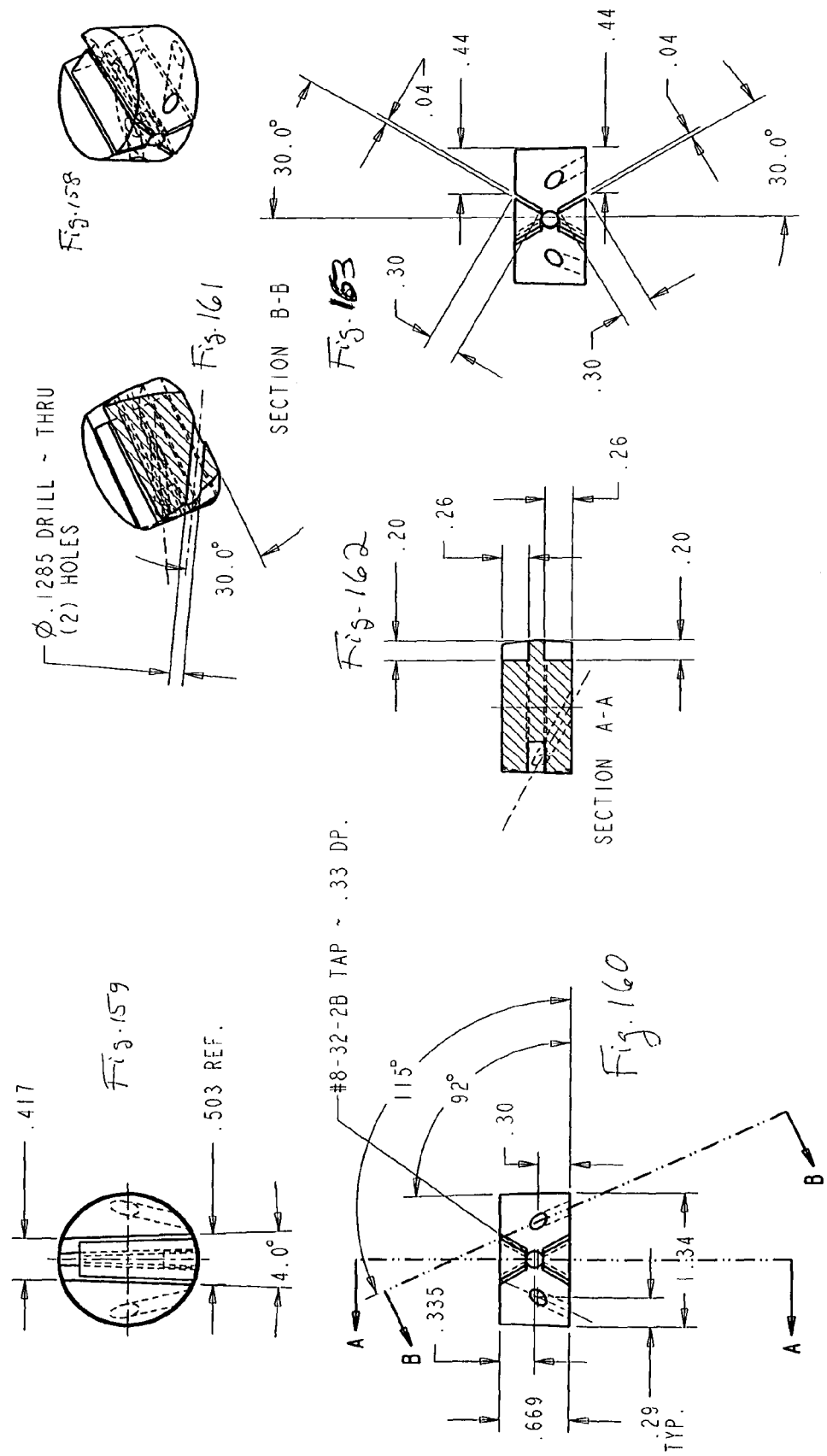

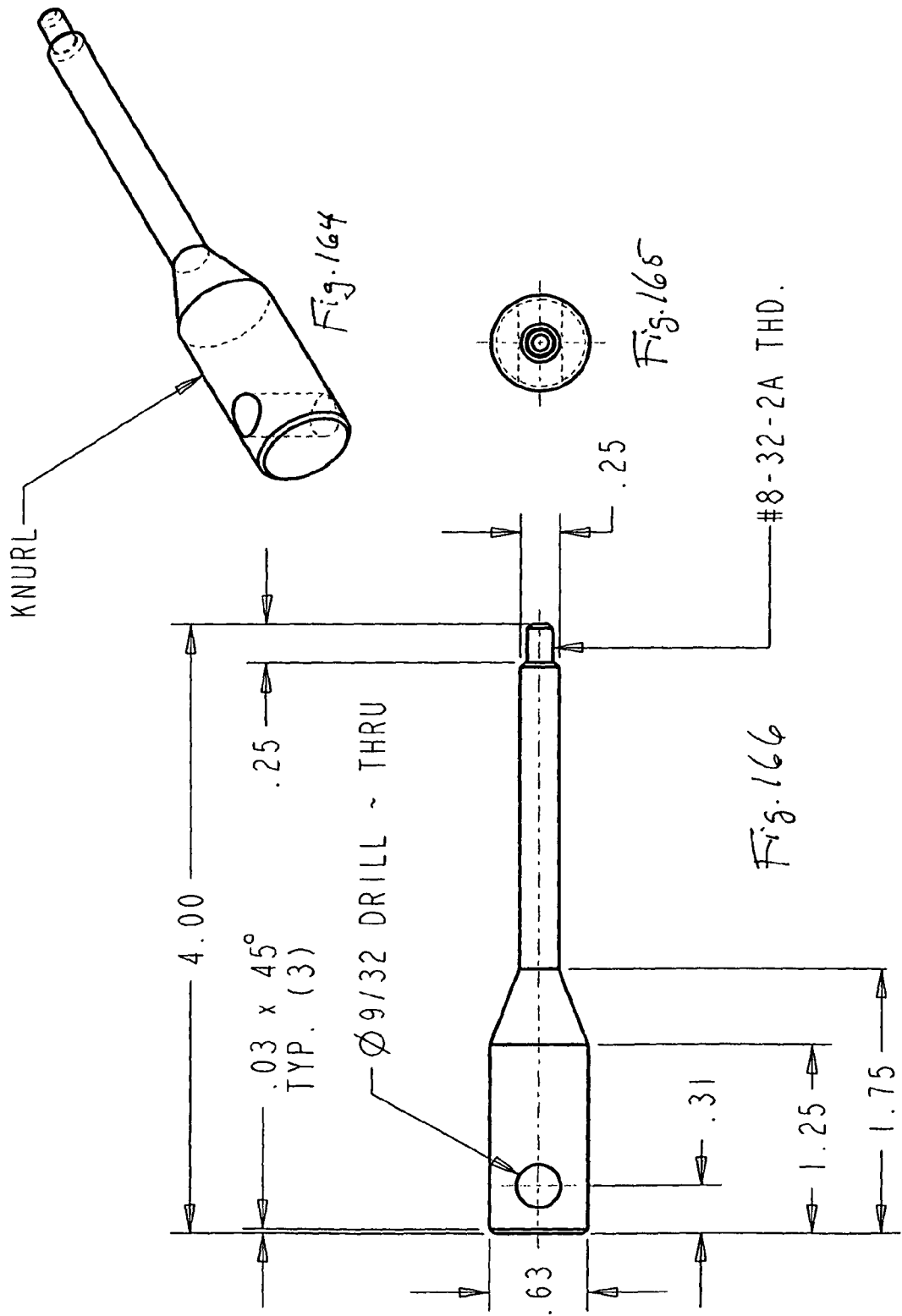

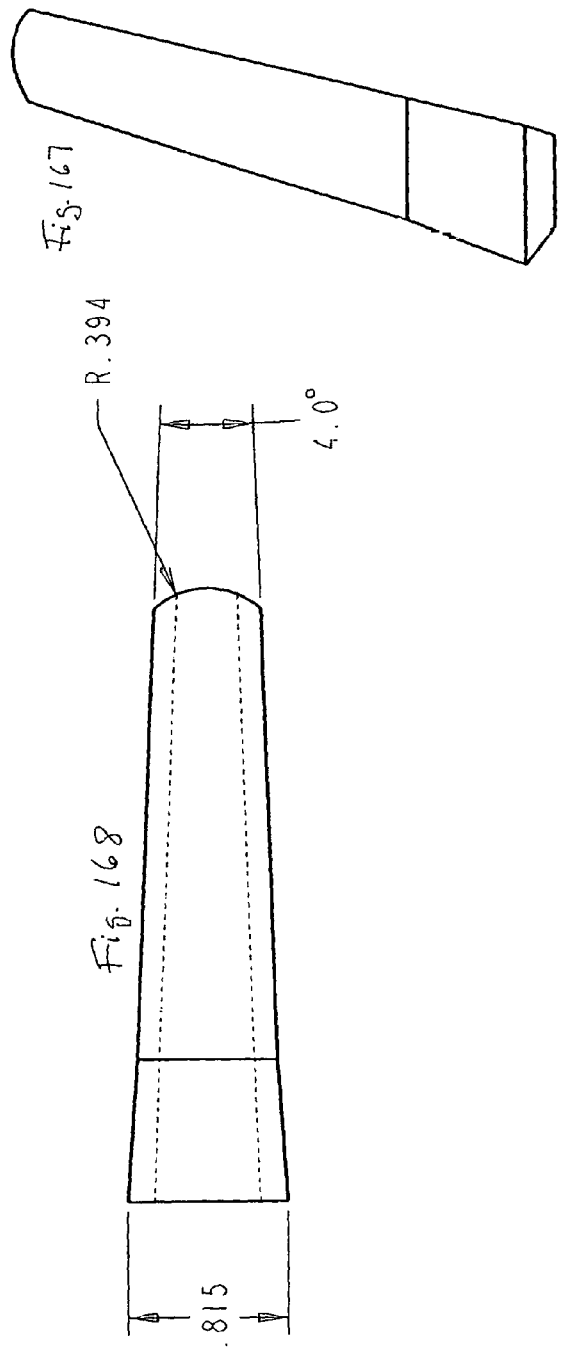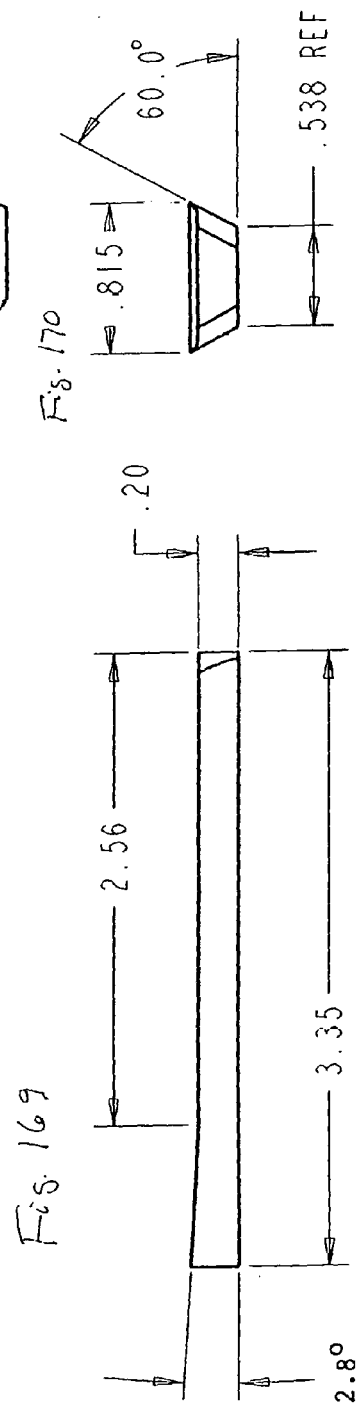
NOTE: ADD RASPS ON EACH OF THE FOUR LONG SIDES OF THE PART VIA EDM BURNING

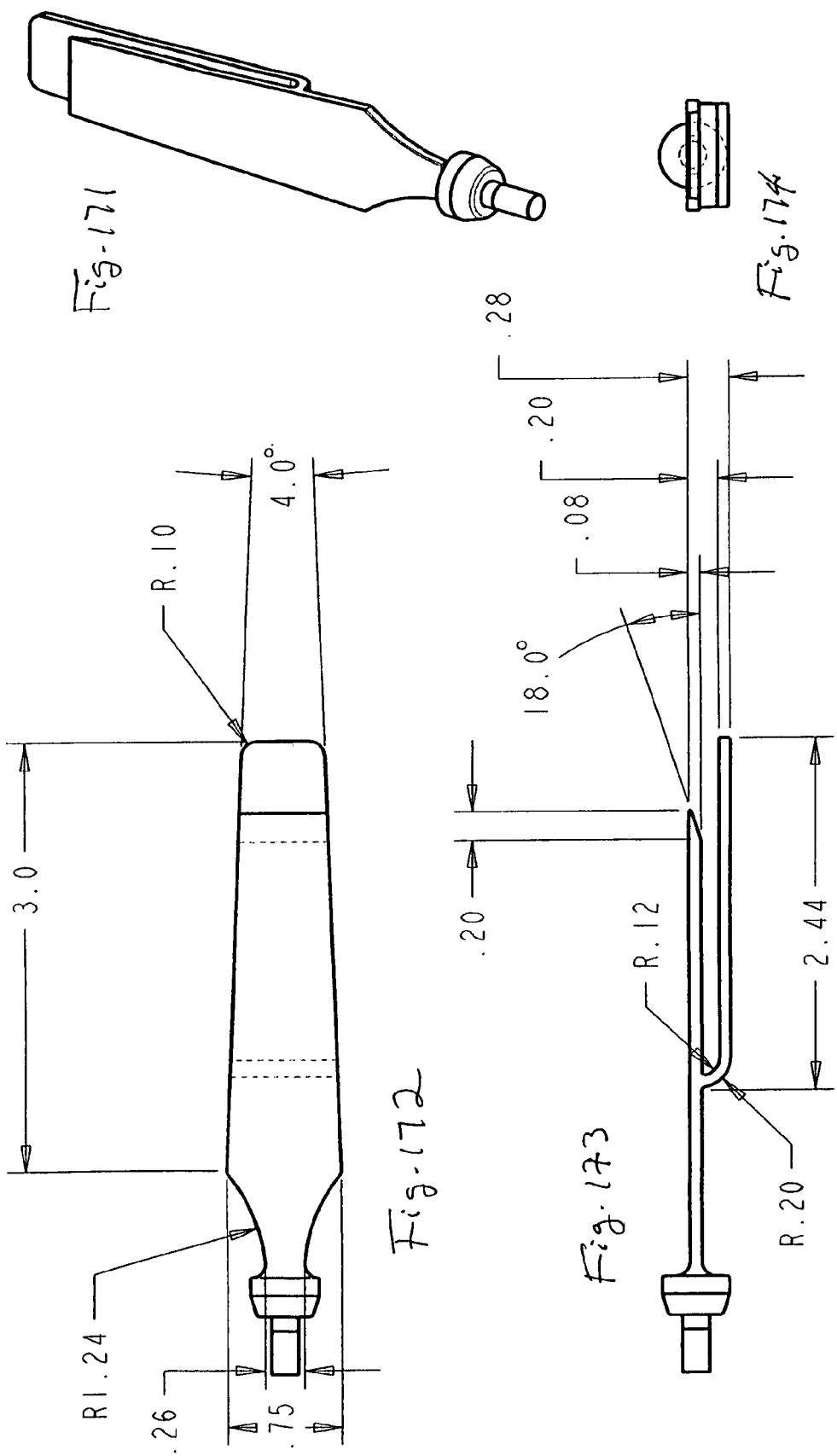

Surgical Procedure (Figs. 175-180)

"eye ball"

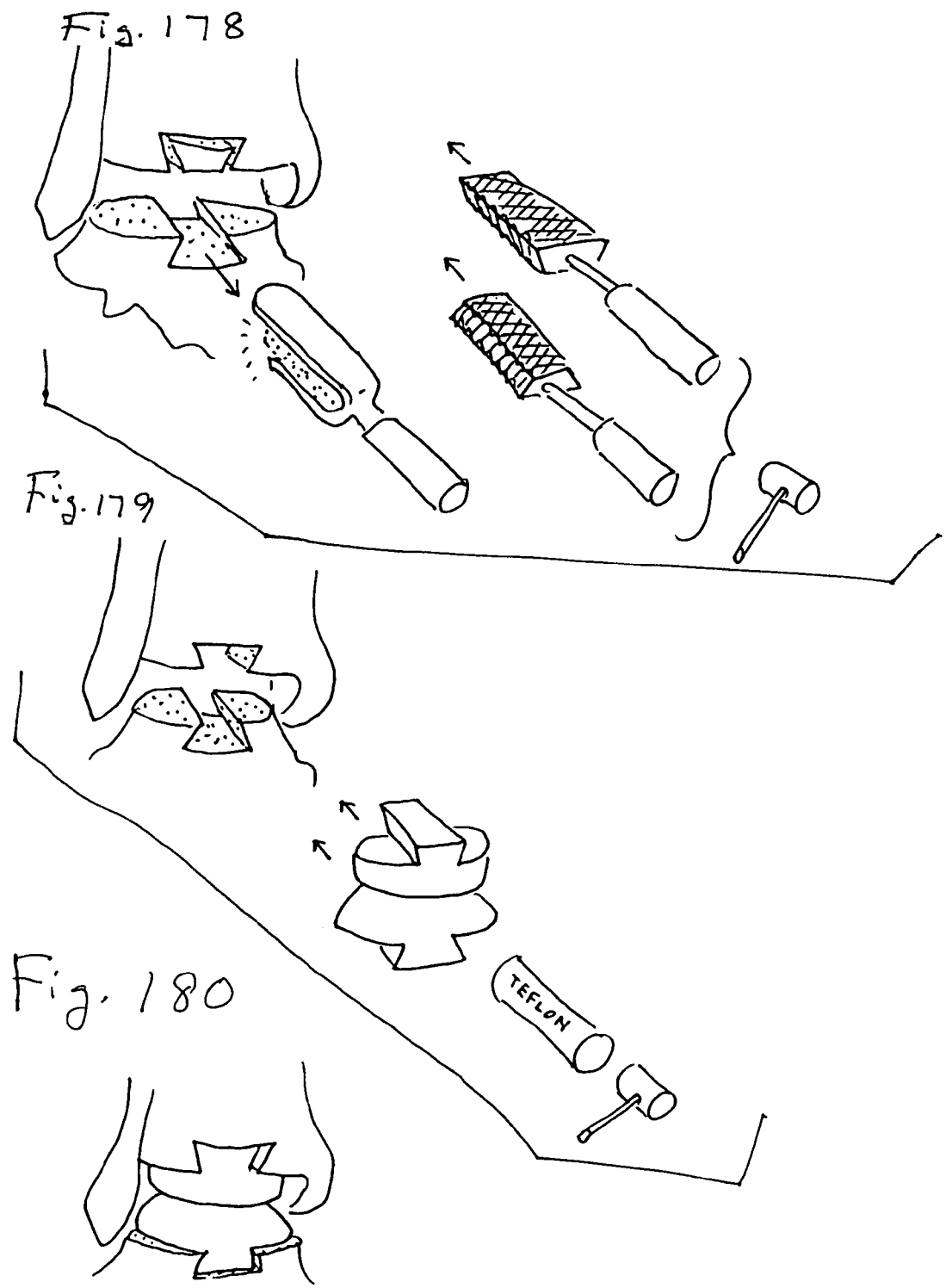

WEDGE-FIXING IMPLANT

This claims the benefits under 35 USC 119(e) of provisional application No. 60/998,198 filed on Oct. 9, 2007 A.D. The complete specification of that application including its drawings is incorporated herein by reference.

FIELD AND PURVIEW OF THE INVENTION

This concerns a prosthetic implant fixable transversely as by a wedge or another laterally disposed feature into a body part. For instance, the implant can be an orthopedic prosthesis, for example, for an ankle, digit, elbow, jaw, kneecap, knee, spinal vertebra, and so forth, and be in a form of a dovetail wedge, which is placed into resected bone stock, and may have away from the noted wedge a further utile feature, for example, a surface for articulation or a part for securement and so forth. Of concern as well are associated surgical templates and other tools for preparation of the body part for the implant. Also of concern are devices connectable with a wedge and receptacle.

BACKGROUND TO THE INVENTION

The Smith Total Ankle, from Wright Manufacturing Company, is a successful prosthetic implant well known to the art. In such a cup and dome implant system, a tibial component has, for example, a stem (fin) that is inserted transversely, in an anterior to posterior direction, into a notch cut in the distal portion of the tibia. As fine a provision as it is, a problem with such an arrangement is that in the insertion of the tibial component, force such as by pounding is employed, and the ankle component with its fin may be pounded inadvertently through and past its intended mark in the tibia.

It would be desirable to ameliorate or even overcome this.

In implants such as for the hip and shoulder, Morse or other tapers intraprosthetically connect ball and stem components.

FURTHER DISCLOSURE OF THE INVENTION

In the genesis of this invention, it has been found that a root of the problem associated with insertion of the prior art total ankle implant is the fact that its fin has substantially parallel sides. Little if anything intrinsically provides for sufficient resistance to consistently stop that implant at the desired stop point along its journey in the resected bone. It is the surgeon's "feel" during pounding that implant into place that is critically relied upon. Such drawbacks have repercussions not only for the ankle, which can be serious enough, but, if a fin of such a configuration were to be provided in an implant for application elsewhere in the body, for an illustration, in a vertebral implant for the spine, and by its pounding it were to shoot past its intended mark, even more serious repercussions could result, as, for illustrative example, damage to spinal nerves and consequent impairment or even death.

And so, in general, the present invention provides an implant comprising an implant body; and connected to the body, a fin type stem adapted for transverse insertion into a bodily substrate, wherein the stem has a laterally disposed feature for providing stopping of the stem along a path it takes in its insertion into the substrate. The implant may have away from the noted fin type stem a further utile feature, which may include a surface for articulation or a part for securement. Provided as well are various associated surgical templates and other tools for preparation of the bodily substrate for the implant. Manufactured articles may be provided in a kit.

The invention is useful in surgery, especially orthopedics.

Significantly, by the invention, problems in the art are ameliorated if not overcome. The present implant intrinsically provides for sufficient resistance to consistently stop it at a desired stop point along its journey in the bodily substrate, for example, resected bone. Accordingly, a more precise and uniform placement of transversely implanted implants is provided, leaving less to be required of each surgeon and his "feel" for driving such implants into position. In turn, transversely inserted, fin type implants can now be more reliably provided for not only the ankle but other parts of the body, for example, spinal vertebrae, and so forth, body parts that are not amenable to stem fixation. The implants of the invention can be very securely held from the outset in bone stock, thus providing for excellent post-surgical recovery and mobility, and surgical cement may be avoided. The invention can be efficiently made and used.

Numerous further advantages attend the invention.

The drawings form part of the specification hereof. With respect to the drawings, which are not necessarily drawn to scale, the following is briefly noted:

FIG. 1 is a whimsical illustration comparing and contrasting a male portion of a Morse taper for an implant stem and what is termed a "Smith wedge" implant, i.e., between a certain area of prior art and a preferred embodiment of the present invention.

FIG. 2 is a side plan view, in an anterior to posterior direction, of an ankle prosthetic implant component of the present invention.

FIG. 3 is a bottom plan view, in a distal to proximal direction, of the implant of FIG. 2.

FIG. 4 is a side plan view, in a lateral to medial direction, of the implant of FIG. 2.

FIG. 5 is a top perspective view of the implant of FIG. 2.

FIG. 6 is a bottom perspective view of the implant of FIG. 2.

FIG. 7 is a side plan view, in an anterior to posterior direction, of a taler prosthetic implant component hereof.

FIG. 8 is a top plan view, in a proximal to distal direction, of the implant of FIG. 7.

FIG. 9 is a side plan view, in a lateral to medial direction, of the implant of FIG. 7.

FIGS. 10 and 11 are top perspective views of the implant of FIG. 7.

FIG. 14 is a side plan view, in an anterior to posterior direction, in array form, of some total ankle replacement joint implant sets of the invention in alternative, mix-and-match ankle and taler prosthetic implant components such as from FIGS. 2-13.

FIG. 15 is a side plan view, in an anterior to posterior direction, of a template for tibial bone resection for an ankle prosthesis implant component in the practice of the invention.

FIG. 16 is a top plan view, in a proximal to distal direction, of the template of FIG. 15.

FIG. 17 is a side plan view, in a lateral to medial direction, of the template of FIG. 15.

FIG. 18 is a top perspective view of the template of FIG. 15.

FIG. 19 is a side plan view, in an anterior to posterior direction, of a template for taler bone resection for a taler prosthesis component for a total ankle implant hereof.

FIG. 20 is a top plan view, in a proximal to distal direction, of the template of FIG. 19.

FIG. 21 is a side plan view, in a lateral to medial direction, of the template of FIG. 19.

FIG. 22 is a top perspective view of the template of FIG. 19.

FIGS. 23-32 are plan views, which can be taken in sequence, depicting a total ankle joint implant as from FIGS. 2-14 and so on, and its implantation by using the templates as of FIGS. 15-22 and other surgical tools, which can include trial components, K-wires, a saw, and shims.

FIGS. 34-129 depict various further embodiments of the invention, embodied as implants for the ankle and associated tools for more efficient preparation of the ankle bones and implantation of the implant components. Regarding these, note the following:

| Figures | Embodiment | Material |
|---|---|---|
| 34-37 | Ankle implant talar component | E.g., cobalt chrome |
| 38-41 | Ankle implant tibial component | 17-4 stainless steel |
| 42-45 | Ankle implant talar component, tall version | Cobalt chrome |
| 46-49 | Ankle implant tibial component, tall version | Cobalt chrome |
| 50-57 | Ankle implant talar cutting guide | 17-4 stainless steel |
| 58-65 | Ankle implant talar cutting guide (deficient tibia) | 17-4 stainless steel |
| 66-73 | Ankle implant talar cutting guide (deficient talus) | 17-4 stainless steel |
| 74-81 | Ankle implant talar cutting guide (deficient talus and tibia) | 17-4 stainless steel |
| 82-88 | Ankle implant tibial cutting guide | 17-4 stainless steel |
| 89-95 | Ankle implant tibial cutting guide (deficient tibia) | 17-4 stainless steel |
| 96-102 | Ankle implant tibial cutting guide (deficient talus) | 17-4 stainless steel |
| 103-109 | Ankle implant tibial cutting guide (deficient talus and tibia) | 17-4 stainless steel |
| 110-113 | Ankle implant broach body | 17-4 stainless steel |
| 114-116 | Ankle implant manipulation tool | 17-4 stainless steel |
| 117-120 | Ankle implant tool, osteotome - section A | 17-4 stainless steel |
| 121-123 | Ankle implant manipulator | 17-4 stainless steel |
| 124-125 | Ankle implant manipulator screw | 17-4 stainless steel |
| 126-129 | Ankle implant dove-tail fitting tool | 17-4 stainless steel. |

FIG. 130 depicts a further embodiment of the invention in which a manufactured device or part with a "Smith" wedge is mated with another manufactured device or part that has a corresponding female receptacle for the wedge. In this figure, a modular stem and tibial tray system for a tibial component for a total knee replacement implant is depicted according to such a principle.

FIGS. 131-133 depict another embodiment of the invention, detailed as a disc replacement set for a disc for the spine.

Figure 143:
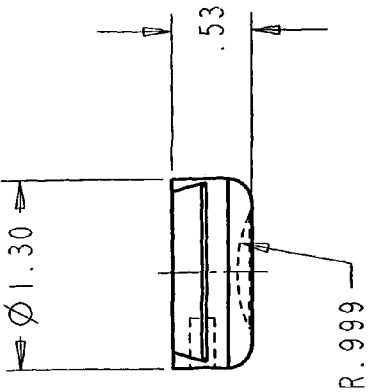
Figure 144:
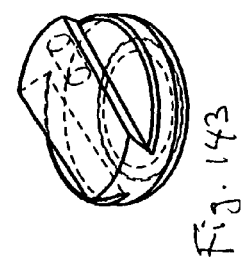
Figure 145:
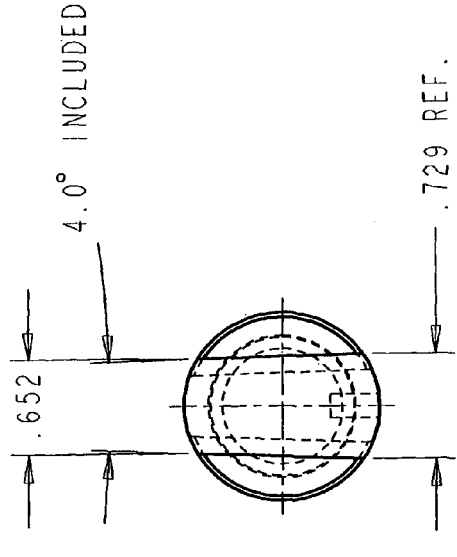
Figure 146:
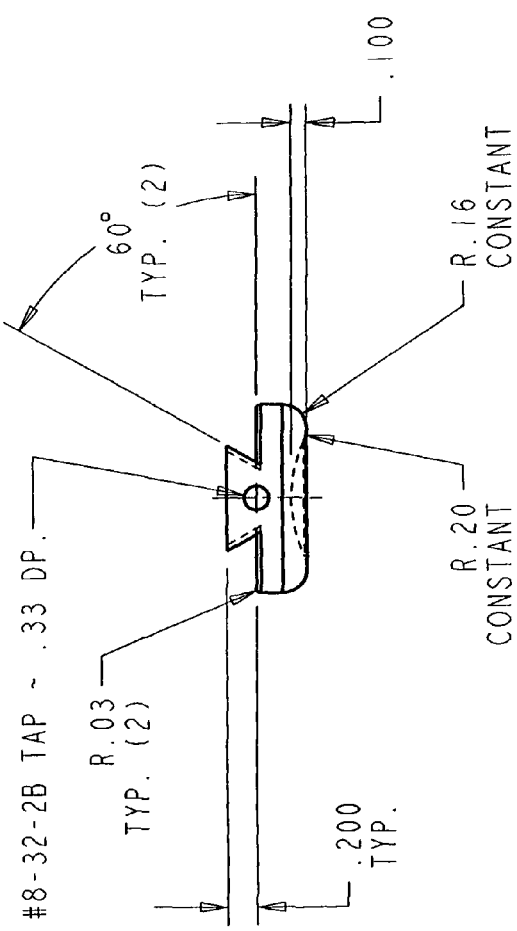
Figures 152, 153:
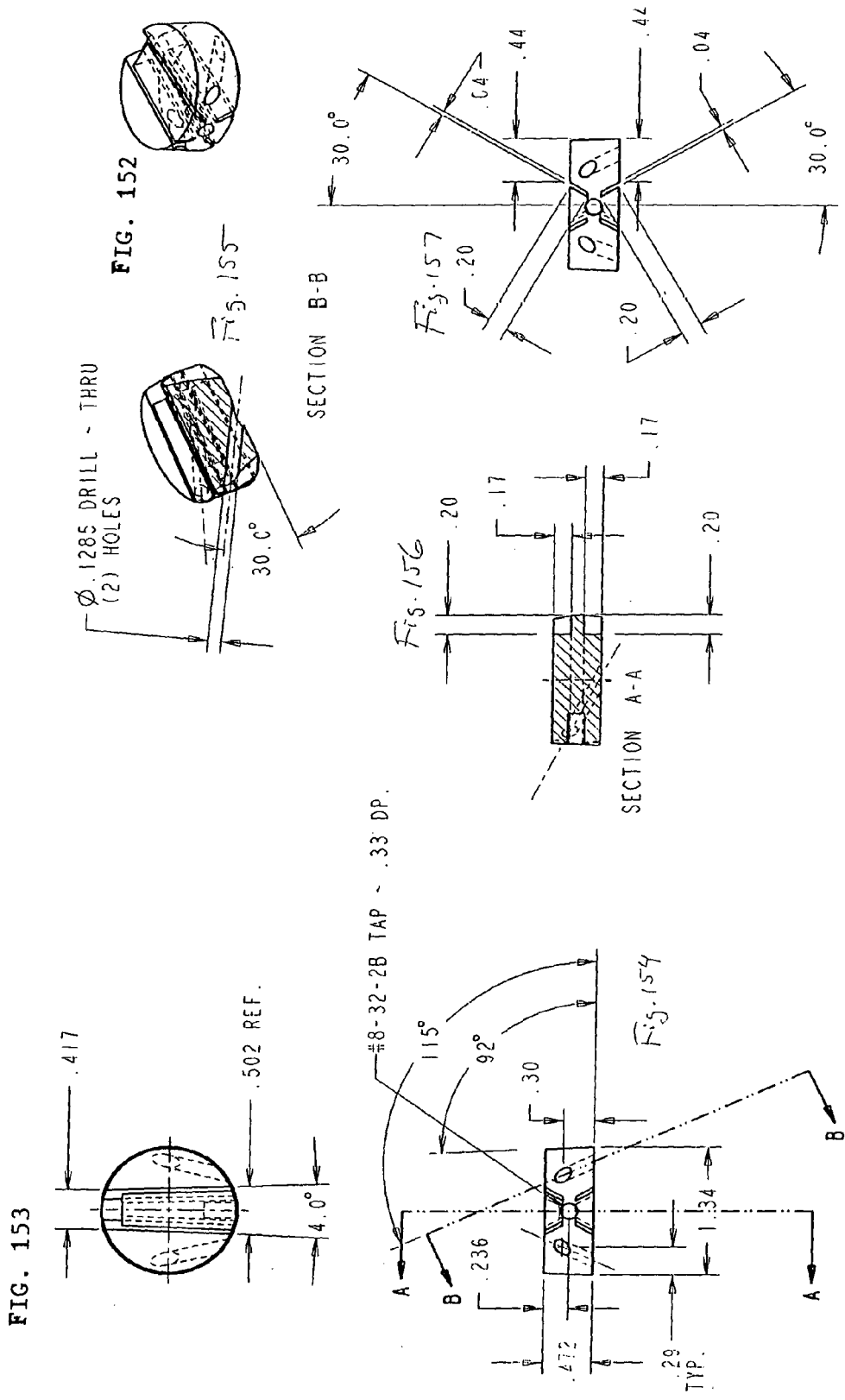
Figure 175:
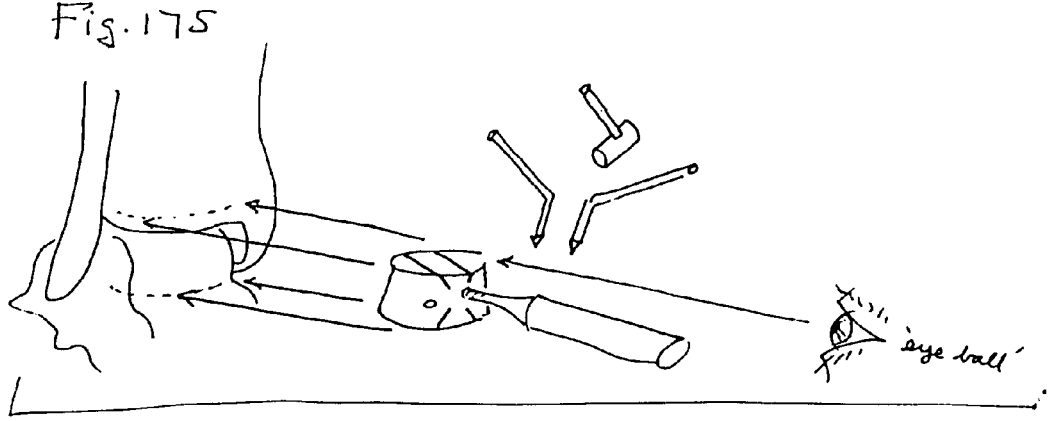
Figure 176:
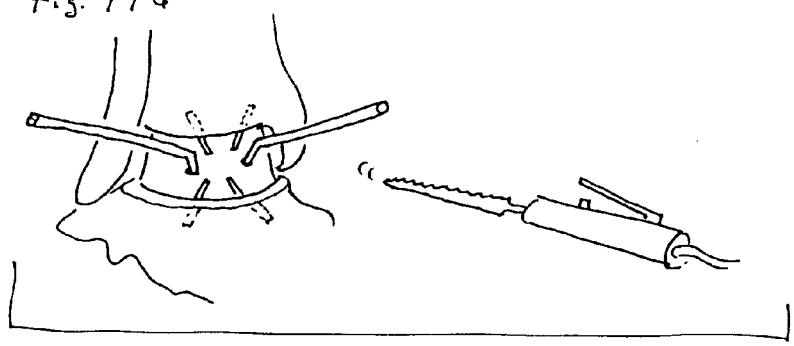
Figure 177:
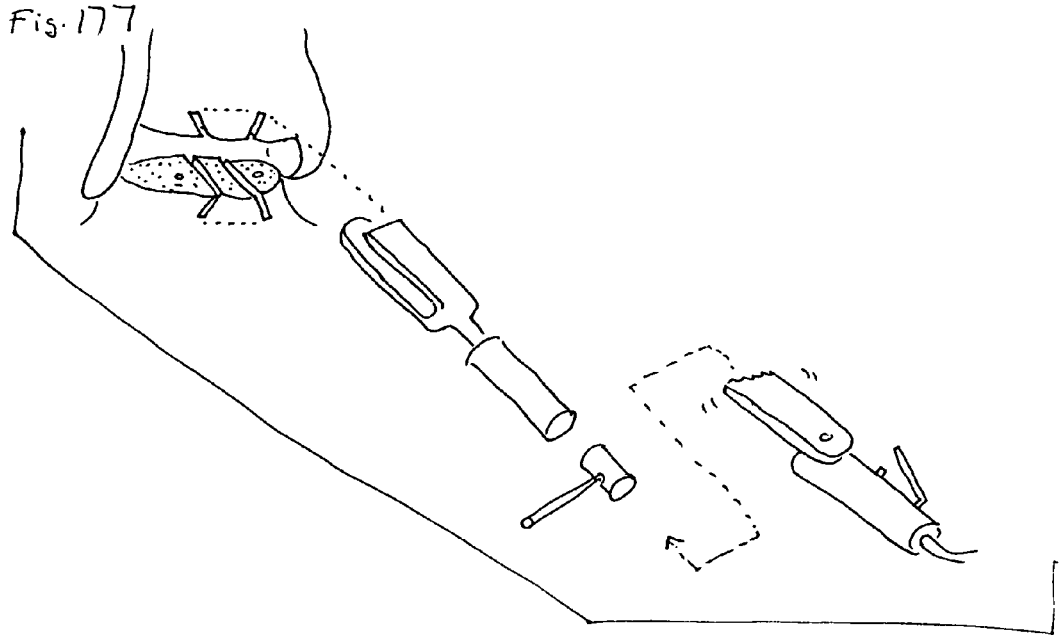

FIGS. 134-180 depict further embodiments of the invention. Regarding these, note the following:

| Figures | Embodiment | Material |
|---|---|---|
| 134-137 | Ankle implant, tibial implant | Cobalt chrome |
| 138-141 | Ankle implant, talar implant | Cobalt chrome |
| 143-146 | Ankle implant, tall tibial implant | Cobalt chrome |
| 147-151 | Ankle implant, tall talar implant | Cobalt chrome |
| 152-157 | Ankle implant, double guide | 17-4 stainless steel |
| 158-163 | Ankle implant, tall double guide | 17-4 stainless steel |
| 164-166 | Ankle implant, doctor installation tool | 17-4 stainless steel |
| 167-170 | Ankle implant, broach body | 17-4 stainless steel |
| 171-174 | Ankle implant tool, osteotome - section A | 17-4 stainless steel |
| 175-180 | Ankle implant, surgical procedure. | |

The invention can be further understood by the detail set out below, which may be read in view of the drawings. Such is to be taken in an illustrative and not necessarily limiting sense.

Key to the present invention is the fin type stem, which has the laterally disposed feature to provide for stopping of the stem along a path it takes in its transverse insertion into the bodily substrate. The laterally disposed feature may take any suitable form, to include, for example, a wedge, especially in a dovetail configuration; a shoulder; and so forth and the like.

The optional further utile feature away from the noted fin type stem can include a surface for articulation or a part for securement. As to the former, i.e., the articulation surface, convex or concave surfaces may be provided, to include those having a shape substantially if not essentially of a truncated hemisphere or another shape that may conform to a natural articulation surface of the body as in a hemiarthroplasty or to the other main component as in a total replacement implant joint for total joint arthroplasty, which other shapes generally may include truncated cylinders, ellipsoids, ovoids, and so forth and the like. As to the latter, i.e., the securement part, a second wedge, a cone, clip, threaded hole, threaded stud, and so forth and the like may be provided to secure another body part or further implant component, and may provide for modularity.

As for the bodily substrate, bone stock is preferred.

The present implant and its tools for surgical implantation can be made of any suitable material(s). For instance, the implant or implant part may be made of a suitable ceramic such as an alumina or a magnesium oxide stabilized, tetragonally toughened zirconia; a metal such as a cobalt-chrome alloy, a stainless steel, or a titanium alloy; and/or a plastic such as an ultra high molecular weight polyethylene, a nylon, or a polyurethane. Likewise, the tools to include templates may be made of such a suitable ceramic, metal and/or plastic. Metal implants may be advantageously provided.

Methods and processes known in the art can be employed to make the implant and its tools. For instance, as known to persons skilled in the art, among many various techniques, a ceramic implant or implant part can be made by machining, firing, and polishing; metal, by casting, forging or machining, and polishing; plastic, by molding and/or machining. A rough or porous coating may be provided by molding, machining or vapor deposition, and so forth. The tools may be made similarly. Other suitable techniques may be employed.

With reference to the drawings, implant 100 can be adapted for implanting in bodily substrate 7, for example, human bone 7B.

The implant 100 may be of the load-bearing type such as for an articulating joint or body subsystem such as the spine. The implant 100 includes implant body 10; and a fin type stem 20, which is connected to the body 10 and is adapted for transverse insertion into the substrate 7/7B.

The body 10 may also have connected thereto and away from the stem 20 further utile feature 12, which may include articulation surface 12A and/or securement part 12S. Substrate-interfacing element 14 may be present, depending on the configuration of the implant, away from so as not to interfere with any operation of the further utile feature 12. A securing pin-receiving hole 15, which may be include threads 15T, may be provided further.

The stem 20 includes laterally disposed feature 22, which has leading element 22L with a lateral dimension that is thinner than that of pursuing element 22P, which trails the leading element 22L in insertion of the implant 100 into the substrate 7/7B. Among the laterally disposed features are noted shoulder 22S and wedge 22W, especially dovetail wedge 22WD. The wedge 22W provides at least lateral holding force in the substrate 7/7B, and the dovetail wedge provides not only lateral holding force but also plumb holding force, i.e., in general, force orthogonal to the plane of the lateral holding force, in the substrate 7/7B, particularly through its intrinsically provided "overhang." The wedge 22W or dovetail wedge 22WD may be provided with any suitable angle from the leading to pursuing elements 22L, 22P; for instance, an angle may be selected from those in the range about or exactly from one to ten degrees, to include two to seven degrees, and three to five degrees, for example, about or exactly four degrees. Thus by the laterally disposed feature 22 (which may include 22L, 22P, 22S, 22W and/or 22WD) the stem 20 can be intrinsically stopped in the path it takes in insertion into the substrate 7/7B, notably in a desired location. Advantageously as well, the implant 100 through the stem 20 can be held in place thereby. In addition, securing pin 25, which may include threads 25T may be present; such may be inserted into and cooperate with the hole 15 and threads 15T to provide further securement of the implant 100. A surgical cement such as polymethylmethacrylate and so forth and the like may be employed if desired.

Rough or porous coating 30 may be provided all or a part of the substrate-interfacing element 14 and/or stem 20. As is known in the art, the coating 30, in general, can engender ingrowth of bony and/or fibrous tissue.

Figure 12:
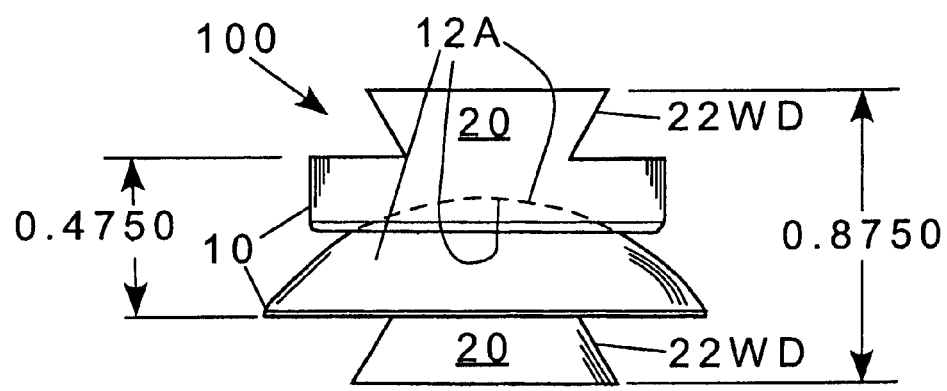
FIG. 12 is side plan view, in an anterior to posterior direction, of the implant components of FIGS. 2 and 7, cooperating in a total ankle replacement joint implant.
Figure 13:
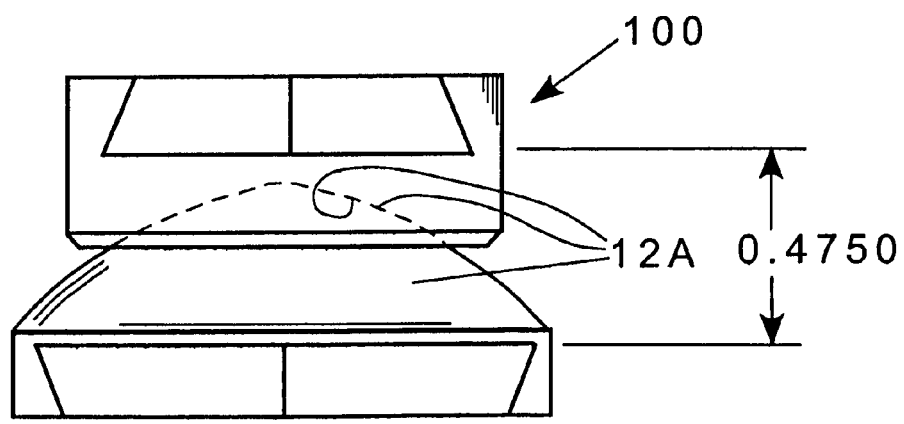
FIG. 13 is side plan view, in a lateral to medial direction, of the replacement joint implant of FIG. 12.
Figure 33:
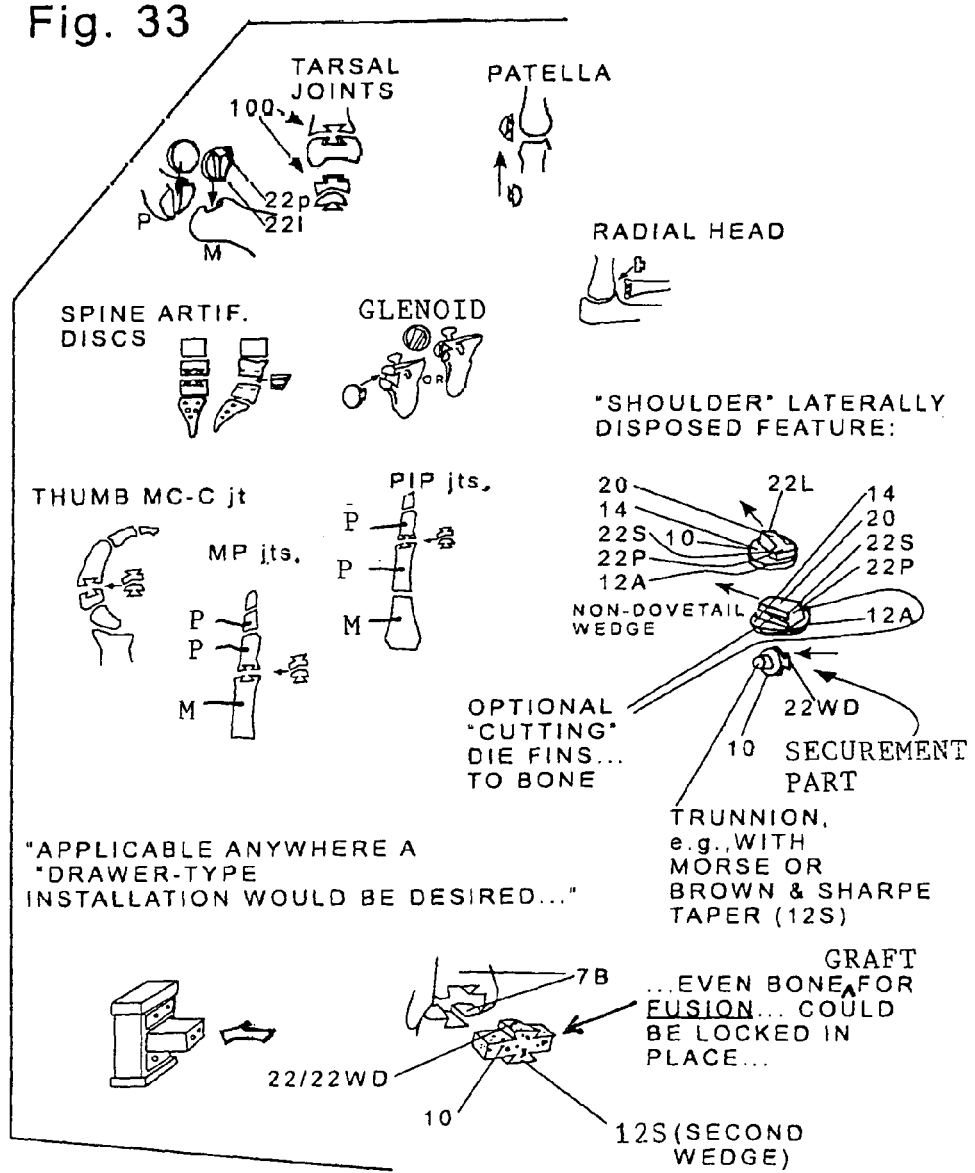
FIG. 33 depicts various further embodiments of the invention.
Figure 35:
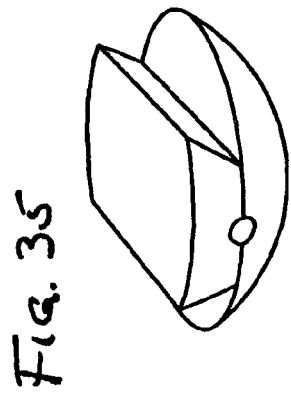
Figure 34:
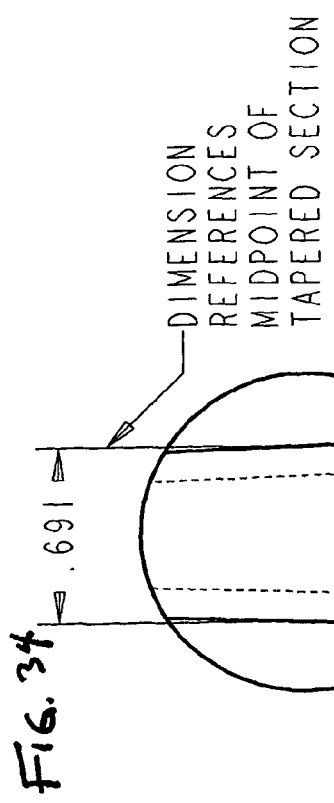
Figure 37:
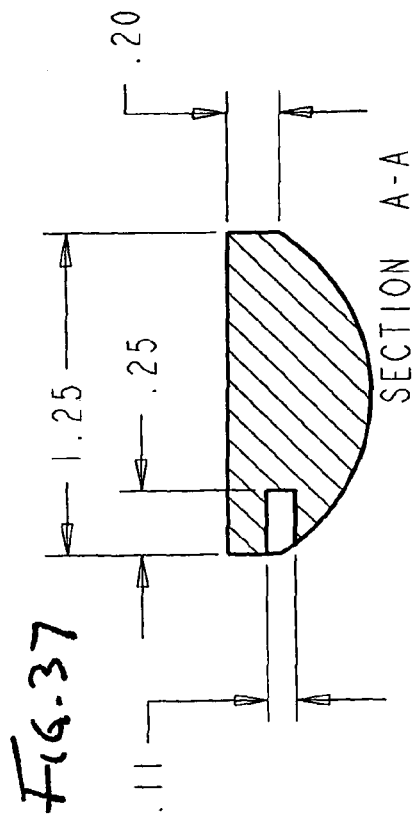
Figure 36:
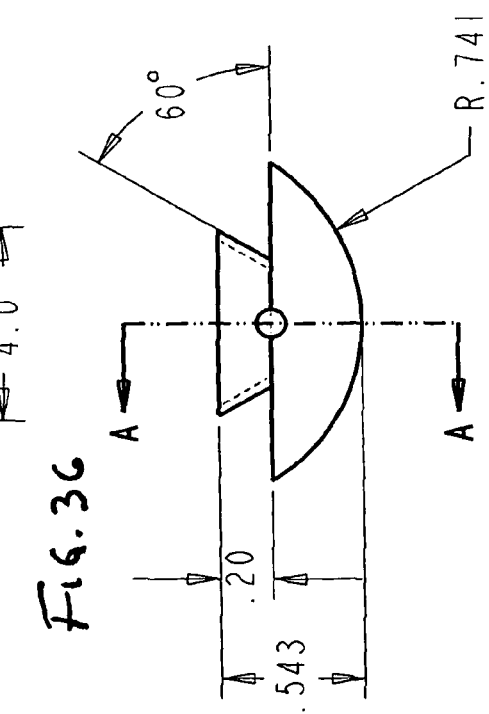
Figure 43:
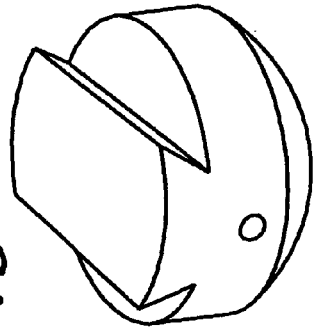
Figure 45:
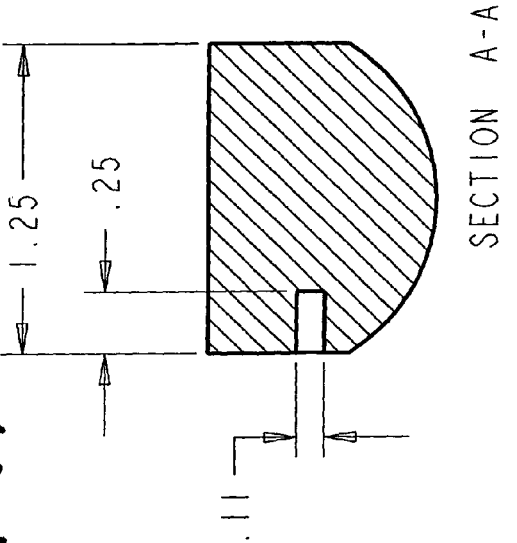
Figure 42:
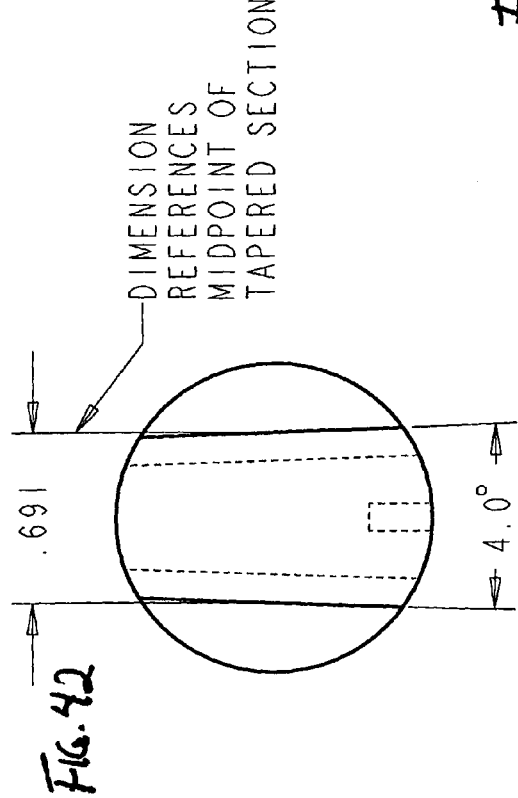
Figure 44:
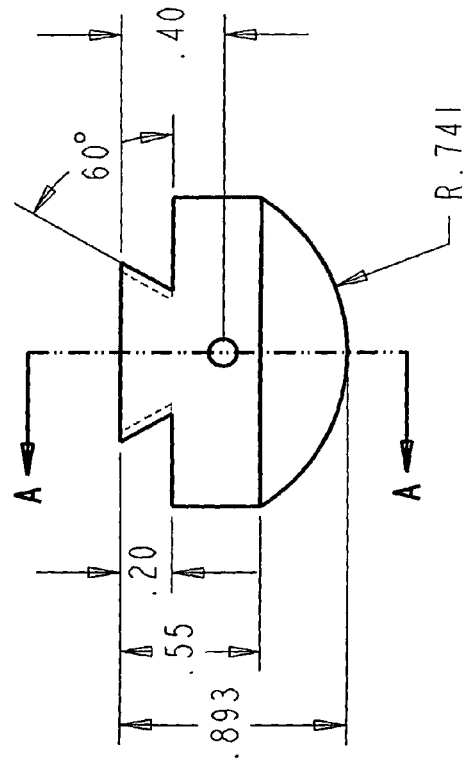
Figure 46:
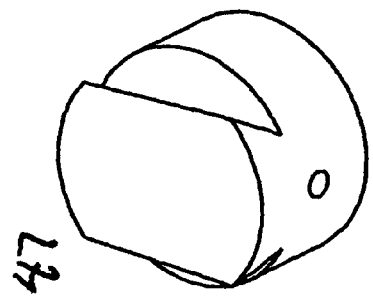
Figure 47:
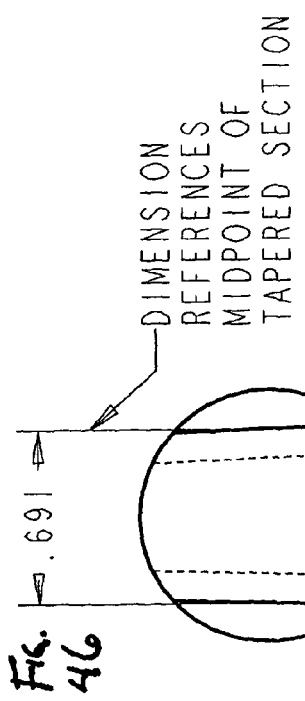
Figure 49:
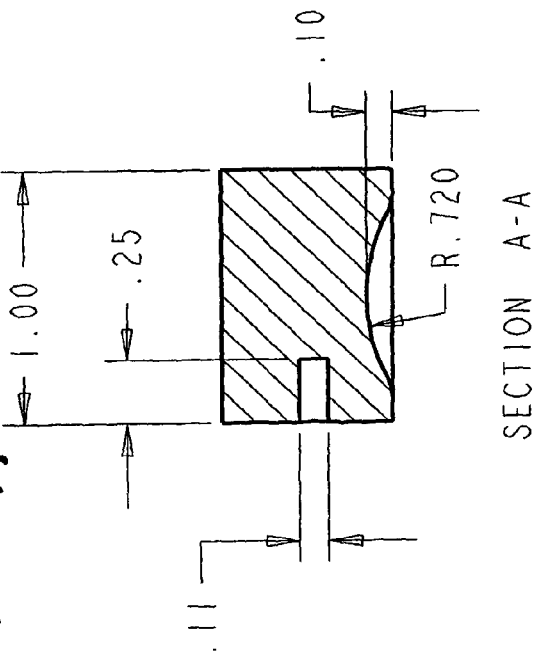
Figure 48:
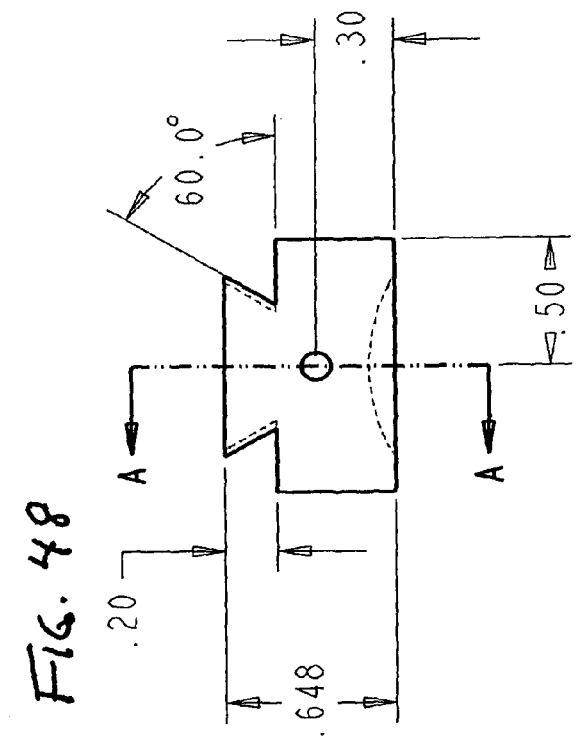
Figure 115:
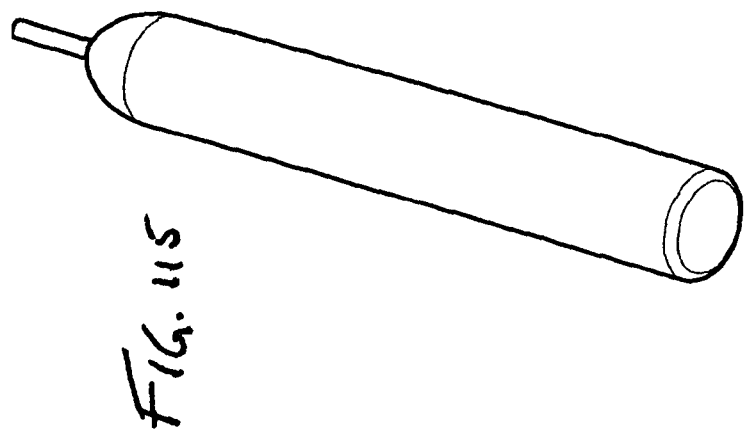
Figure 116:
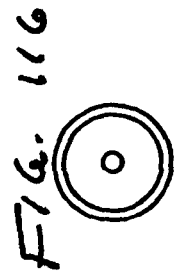
Figure 114:
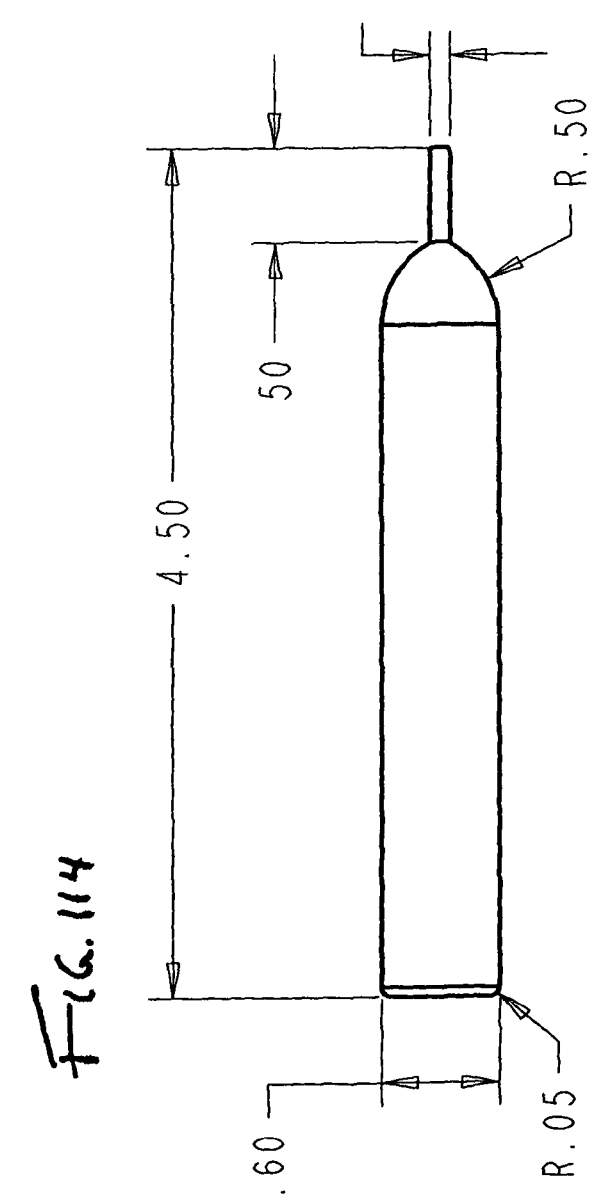
Figure 122:
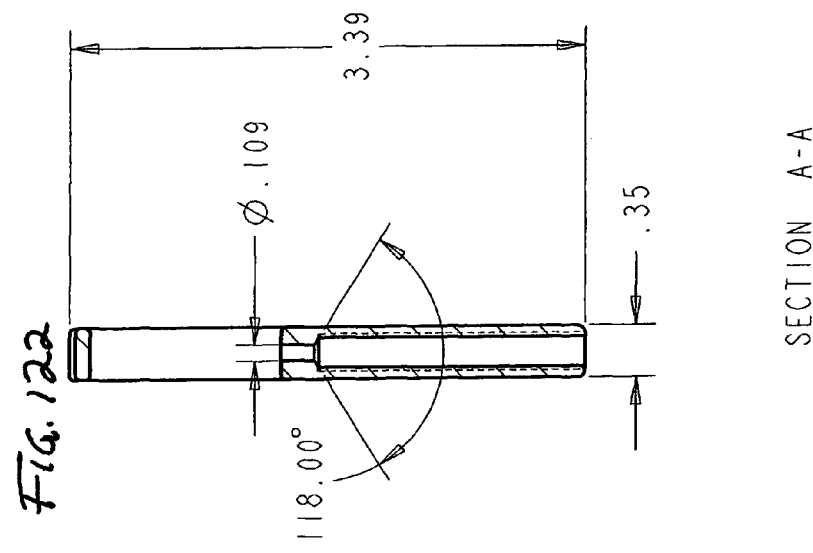
Figure 121:
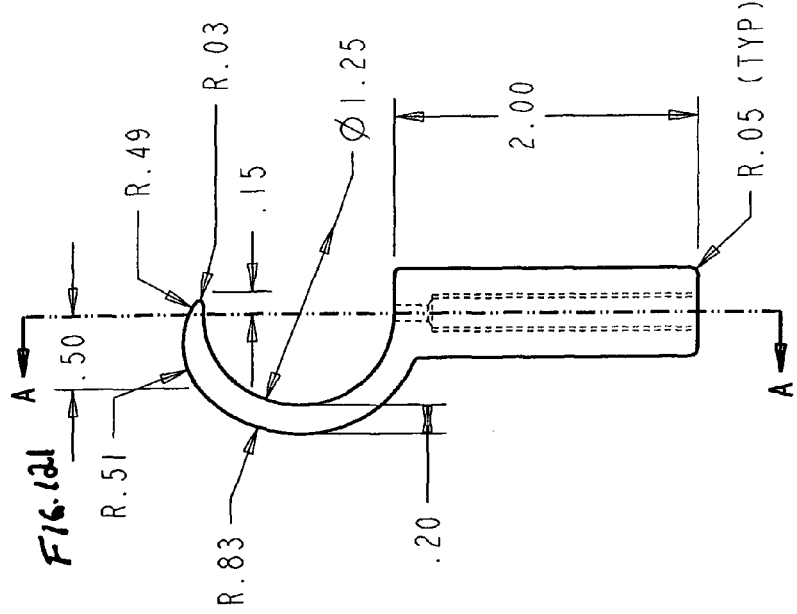
Figure 123:
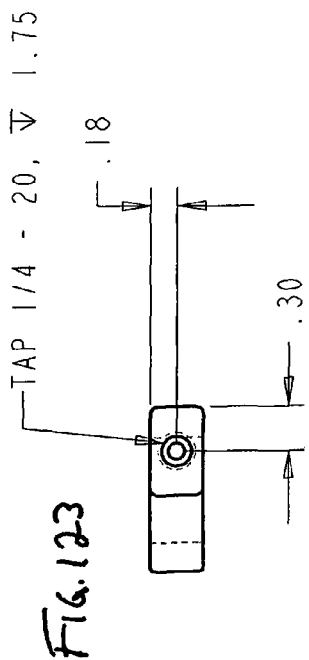
Figure 124:
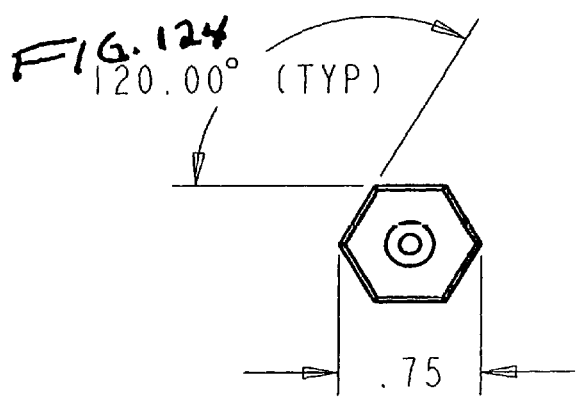
Figure 125:
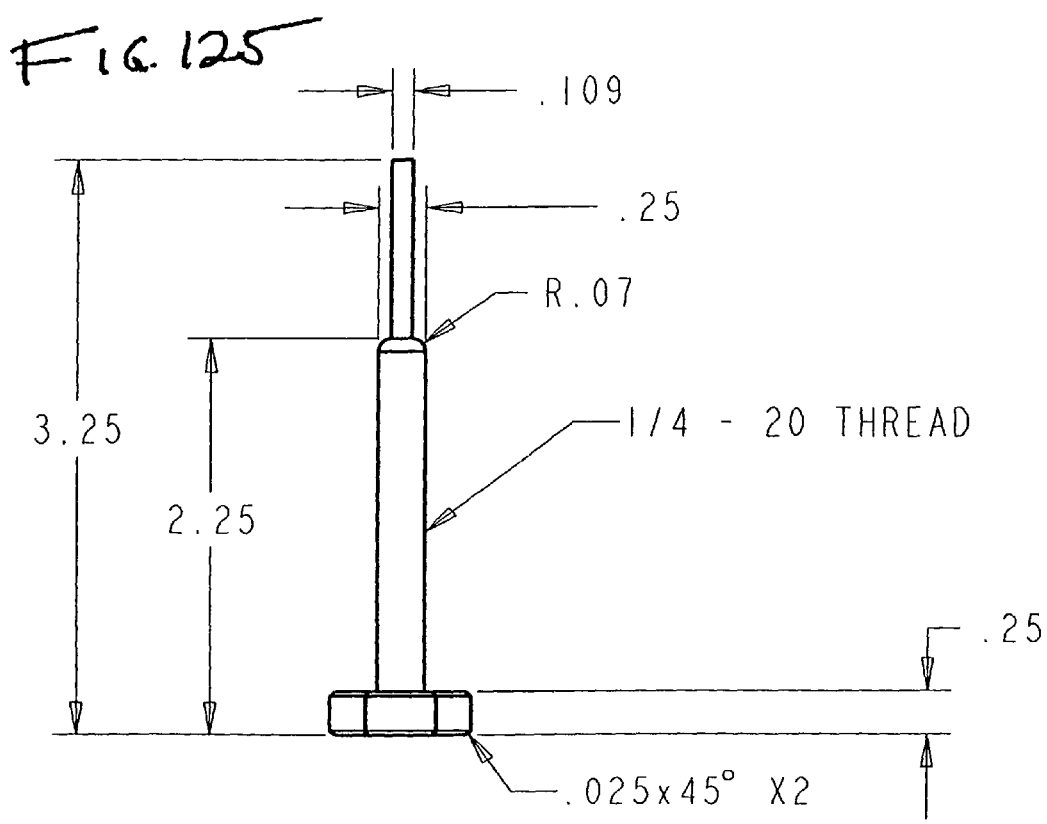

Thus, the implant 100 is provided. See, FIGS. 2-14, 33 and 130-133. See also, FIGS. 34-49 and 134-151.

Figure 23:
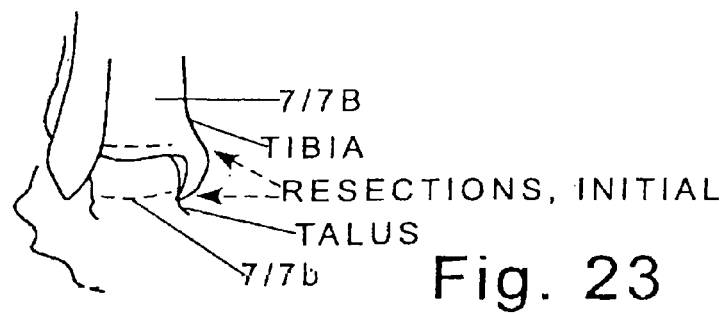
Figure 24:
Figure 25:
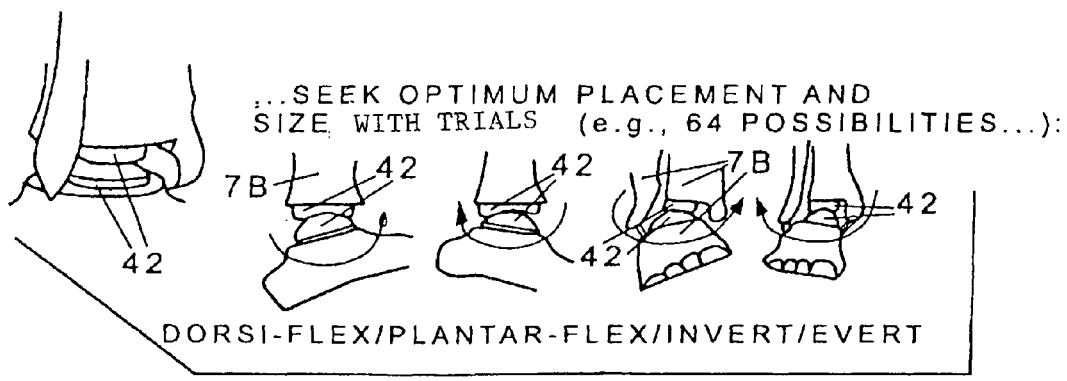
Figure 26:
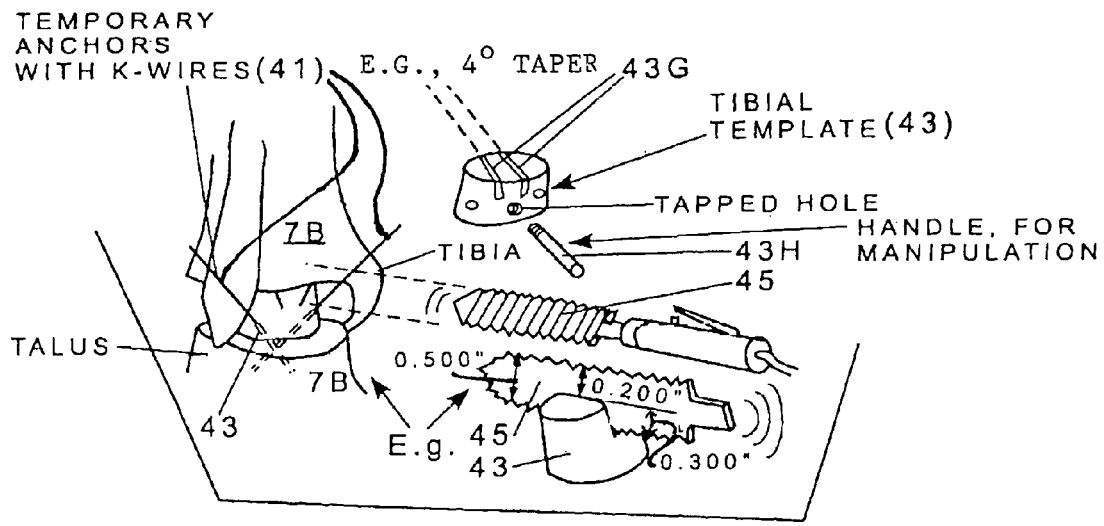
Figure 27:
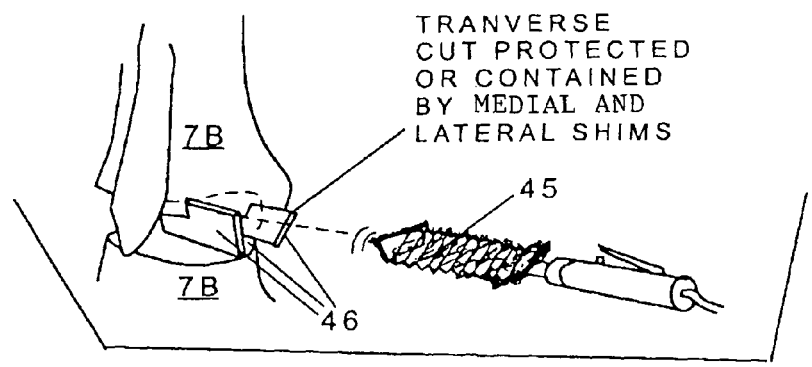
Figure 28:
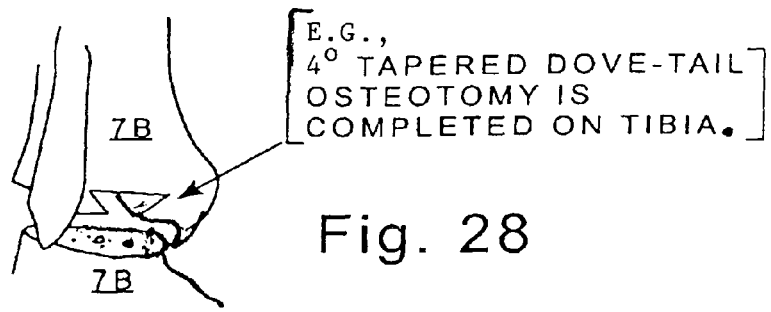

The implant of the invention can be implanted by those of skill in the surgical art, and any suitable method or process can be employed to carry this out. The implant 100, for example, can be implanted with the aid of various tools to include associated surgical tools 40, and such items or parts thereof may be provided in kit form. Among the surgical tools 40, K-wires 41, trial components 42, templates 43 and 44, saw 45, and shims 46 can be employed to advantage, with for instance, for a total replacement joint prosthesis; for example, that of the human ankle, the trial components 42 being tibial and taler trial components; the template 43 being a tibial template dovetail wedge for preparation of bone 7B of the tibia; and the template 44 being a taler template for dovetail wedge preparation of bone 7B of the talus. The templates 43, 44 can include, among other possibilities, body 43B, 44B; saw-guide grooves 43G, 44G; handles 43H, 44H; and component-placement wedge 44W. See, FIGS. 15-22 and 23-32. See also, FIGS. 50-129; 152-174 and 175-180.

In the drawings, numerical values are provided in inches, unless otherwise stated or to be understood by the context. Such numerical values may be considered to be approximate or exact. Regarding FIGS. 34-129 and 134-174, note the following:

Tolerance Chart

Angle +/−1°
0.0 inch +/−0.040 inch
0.00 inch +/−0.020 inch
0.000 inch +/−0.010 inch.

Ankle implant(s) of the invention has(have) been successfully implanted. The first such implant was done in spring 2007 A.D.

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

What is claimed is:

1. An implant or implant component device comprising a load-bearing implant or component therefor, which bears load substantially in a load-bearing direction when implanted, and which includes the following:

at least one implant body, each having connected thereto one and only one transverse stem, which runs in a first transverse direction substantially perpendicular to the load-bearing direction, and which has along the first transverse direction a leading element and a pursuing element, with:
the leading element having and terminating in one and only one wall projecting from the at least one implant body, which has a lateral or radial dimension along a second transverse direction essentially perpendicular to the first transverse direction and substantially perpendicular to the load-bearing direction that is less than that of the pursuing element,
the pursuing element having and originating in one and only one wall projecting from the at least one implant body, which has a lateral or radial dimension along said second transverse direction but spaced apart from the one and only one wall of the leading element, and
the one and only wall of each of the leading and pursuing elements projects in its entirety substantially perpendicular from the pertinent at least one implant body, and
which one and only one transverse stem has between the leading and pursuing elements two spaced apart side walls projecting from the at least one implant body, wherein said one and only one wall of the leading element and said one and only one wall of the pursuing element each separately connect said two side walls, wherein:
said one and only one wall of the leading element is not greater than a lateral or radial distance between said two side walls about the leading element, and
said one and only one wall of the pursuing element is not substantially greater than a lateral or radial distance between said two side walls about the pursuing element, and
with the one and only one transverse stem adapted for transverse insertion into resected bone configured for complementary female reception of the one and only one transverse stem such that the one and only one transverse stem has a laterally disposed feature for providing stopping of the one and only one transverse stem along a path it takes in its transverse insertion into said bone; and on the at least one implant body, away from and generally opposing the one and only one transverse stem, a surface for articulation.

2. The implant or implant component device of claim 1, wherein the laterally disposed feature for providing stopping of the transverse stem is a wedge.

3. The implant or implant component device of claim 2, wherein the wedge is in a form of a dove-tail wedge such that both lateral and plumb holding forces are provided.

4. The implant or implant component device of claim 3, wherein the at least one implant body is part of an ensemble for total joint arthroplasty of an articulating joint, which has, as the at least one implant body, two implant bodies, each with the one and only one transverse stem adapted for implantation into separate resected bones, each configured for complementary female reception of the one and only one transverse stem such that the one and only one transverse stem has a laterally disposed feature for providing stopping of the one and only one transverse stem along a path it takes in its transverse insertion into said bones, which are resected bones of the joint, and each including the surface for articulation such that the surface for articulation of one of the two implant bodies is complementary to and can articulate against the surface for articulation of the other of the two implant bodies when the ensemble is implanted.

5. The implant or implant component device of claim 4, wherein the device is adapted for an articulating joint of an ankle, which provides for excellent post-surgery recovery and mobility.

6. The implant or implant component device of claim 3, wherein the at least one implant body is adapted for arthroplasty of an articulating joint, with the transverse stem adapted for implantation into said bone, which is resected bone of the joint, selected from the group consisting of a glenoid bone, a patella, a radial head of a long bone other than an ankle, opposing spinal vertebrae, and a digit such that the implant or implant component device is selected from the group consisting of a glenoid implant, a patellar implant, an implant for a radial head of a long bone other than an ankle, a spinal vertebral implant, and a digital implant.

7. The implant or implant component device of claim 1, wherein the at least one implant body is made of a magnesium oxide stabilized, tetragonally toughened zirconia.

8. In combination, in kit form, the implant or implant component device of claim 1, and a resection template tool for preparation of a bodily substrate for implantation of the implant or implant component device, wherein the resection template tool includes a tool body having a substantially thick disc form having a first surface, a second surface for engaging resected bone opposing but not confronting the first surface, and an outer wall boundary connecting the first and second surfaces, and a pair of opposing slots forming grooves in the first surface, which open through the outer wall boundary at two locations, into which a bone saw can be inserted and guided so as to cut bone for configuration of lateral walls in the bone for the complementary female reception of the one and only one transverse stem.

9. An implant device for insertion in a joint having confronting first and second bones, which comprises:

an implant body having a substrate-interfacing element and, on an opposite side of the body but not confronting said element, a working surface configured to face the second bone and to be disposed in a predetermined position relative to the first bone when implanted; and
a transversely elongated stem on the body having leading and pursuing ends for implantation in an elongated, resected passage of the first bone when the elongated, resected passage of the first bone:
projects in a direction transverse to an axis generally perpendicular to the confrontation of the first and second bones;
has respective first and second ends, at least the first end being open;
has two opposing lateral walls, at least one lateral wall of which with a surface facing the first end to provide a laterally disposed feature for providing stopping of a transversely elongated stem having leading and pursuing ends inserted therein, with the leading end thinner laterally than the pursuing end; and
optionally, projects in an anterior to posterior direction;
wherein:
the stem is configured to complementarily fit the resected passage in the first bone, and includes two opposing side walls for respectively engaging the two lateral walls of the elongated, resected passage, with at least one side wall of the two opposing side walls that can engage the aforesaid at least one lateral wall of the elongated, resected passage of the first bone to provide for stopping of the stem therein and to maintain the working surface in a predetermined position when the stem is inserted into the elongated,
resected passage of the first bone from the first end thereof and the working surface is positioned in the predetermined position;
the leading and pursuing ends of the stem are each in a form of a wall that projects in its entirety substantially perpendicular from the substrate-engaging element;
the leading end of the stem is thinner laterally than the pursuing end of the stem;
the two opposing side walls of the stem angle laterally outwardly away from one another from a location by the implant body to a location spaced apart from the implant body so as to form a tapered dovetail configuration; and
the stem is configured to angle the two opposing side walls from the leading end to the pursuing end laterally outwardly away from one another at an angle about from 1 to 10 degrees.

10. The implant device of claim 9, which is made of a magnesium oxide stabilized, tetragonally toughened zirconia.

11. The implant device of claim 9, wherein the stem is configured to angle the side walls laterally outwardly away from one another at an angle about from 2 to 7 degrees.

12. The implant device of claim 11, wherein the angle is about 4 degrees.

13. The implant device of claim 9, wherein the implant body is configured with a convex segment of a sphere defining the working surface.

14. The implant device of claim 9, wherein the implant body is configured with a concave socket defining a segment of a sphere defining the working surface.

15. The implant device of claim 9, which is useful for implanting in an ankle and providing excellent post-surgery recovery and mobility, and wherein the working surface of the implant body is in a form of a segment of a sphere.

16. An ankle arthroplasty implant device comprising:
first and second implant bodies for implanting in respective talar and tibial bones of a patient, the first body including a truncated, convex spherically shaped dome articular surface, and the second body including a truncated, concave spherically shaped socket articular surface for operatively engaging with said dome; and
first and second transversely elongated wedge-shaped stems on respective bodies and having leading and pursuing ends, each of which has one and only one wall projecting from its respective body and in its entirety substantially orthogonal thereto at an outer boundary of said body, and including respective spaced apart side walls angling laterally outwardly away from one another from the respective leading toward the pursuing ends to form respective dovetail configurations.

17. The ankle arthroplasty implant device of claim 16, made of a material selected from the group consisting of a metal and a ceramic.

18. The ankle arthroplasty implant device of claim 17, wherein the outer boundary of said body is substantially circular when viewed from a top or bottom position.

19. The ankle arthroplasty implant device of claim 18, wherein each of said first and second stems is configured to angle the respective spaced apart side walls laterally outwardly away from one another at an angle about from 3 to 5 degrees.

20. A combination comprising, in kit form, (A) a joint prosthesis apparatus for implant at a selected transverse location in an articulating, weight bearing joint space presenting male and female joint components, the joint components having a predetermined transverse width and being formed with respective through, elongated wedge shaped, dovetail, transverse resection channels located at selected positions in the respective joint components and being of a predetermined shape, having opposite dovetail sides converging linearly along their lengths at a selected angle with respect to one another in the transverse direction from respective wide channel openings formed to open to the respective one transverse side of the joint and narrower channel openings formed to open on the transverse side of the joint opposite the one transverse side, the joint prosthesis apparatus comprising:
prosthesis devices to implant in the articulating joint space, each of these having a body with a substrate-interfacing element, with a first of the devices including a truncated concave sphere shaped socket and a second of the devices including a truncated convex sphere shaped ball element to be received complementarily in the socket, wherein the substrate-interfacing element in the first of these devices is opposite but not confronting the socket and the substrate-interfacing element in the second of these devices is opposite but not confronting the ball element,
each of the prosthesis devices including an axial stem configured with opposite dovetail shaped stem side walls diverging linearly away from one another at the selected angle in a transverse wedge shape with a narrow leading end and a wide trailing end and constructed to be received transversely from the respective wide channel openings to be nested in close fit relationship in the respective resection channel to wedge against the side walls of the resected channels located at the selected location such that a surgeon can extend a cutting instrument fully through in the lateral direction across the joint components to cut the resection channels with channel side walls angling toward one another at the selected angle to define the predetermined shape in the joint components,
the devices selected and the stems introduced through the wide openings of the respective channels to be driven transversely into the channels from the wide channel openings to wedge the stems in close fit relationship in the respective channels at the selected location, and (B) at least one template tool to be disposed adjacent the joint components, wherein the at least one template tool comprises a tool body in substantially thick disc form having a first surface, a second surface opposing but not confronting the first surface, and an outer wall boundary connecting the first and second surfaces, the tool body constructed with a pair of guide slots diverging away from one another at the selected angles, each guide slot passing through the first surface and, at two locations, the outer wall boundary, and configured and oriented to receive the cutting instrument to project therefrom to cut the transverse resection channel for the at least one of the joint components for receipt of one of the prosthesis devices configured with the predetermined shape.

21. The combination of claim 20, wherein the joint prosthesis apparatus is useful for implant in a dysfunctional ankle and for providing excellent post-surgery recovery and mobility, replacing tibial and talar joint components, wherein the stems are constructed with respective lateral lengths sufficient, when implanted, to project substantially laterally across transverse widths of the tibial and talar joint components.

22. The combination of claim 21, wherein the at least one template tool includes at least two template tools in substantially thick disc form as aforesaid, at least one of the two of which is further constructed with a dovetail shaped stem projecting from the second surface.

23. The combination of claim 20, wherein the stems of the joint prosthesis apparatus are formed with the stem side walls diverging away from one another at an angle about from 3 to 5 degrees; and the guide slots of the at least one template tool are at a corresponding angle.

24. The combination of claim 23, wherein the stems of the joint prosthesis apparatus are each formed with a width of substantially 0.691 inch for its dovetail shaped stem side walls, referenced for each stem midway between its leading and pursuing ends, and furthest away from its substrate-interfacing element; and the guide slots of the at least one template tool are correspondingly spaced apart.

25. The combination of claim 20, wherein the stems are each formed with stem side walls diverging away from one another at an angle of about 4 degrees, and with a width of substantially 0.691 inch for its dovetail shaped stem side walls, referenced for each stem midway between its leading and pursuing ends, and furthest away from its substrate-interfacing element; and the guide slots of the at least one template tool are at a corresponding angle and are correspondingly spaced apart.

26. The combination of claim 20, wherein the at least one template tool includes at least two template tools in substantially thick disc form as aforesaid, at least one of the two of which is further constructed with a dovetail shaped stem projecting from the second surface.

* * * * *